(12) United States Patent
Kuroda et al.

(10) Patent No.: US 7,851,187 B2
(45) Date of Patent: Dec. 14, 2010

(54) METHOD OF PRODUCING L-SERINE DERIVATIVE AND ENZYME USED THEREFORE

(75) Inventors: Shinji Kuroda, Kawasaki (JP);
Hiroyuki Nozaki, Kawasaki (JP);
Kunihiko Watanabe, Kawasaki (JP);
Kenzo Yokozeki, Kawasaki (JP); Yuki Imabayashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 134 days.

(21) Appl. No.: 11/942,873

(22) Filed: Nov. 20, 2007

(65) Prior Publication Data

US 2009/0170171 A1    Jul. 2, 2009

Related U.S. Application Data

(63) Continuation of application No. PCT/JP2006/309949, filed on May 18, 2006.

(30) Foreign Application Priority Data

May 20, 2005    (JP) .............................. 2005-148660

(51) Int. Cl.
| | |
|---|---|
| C12P 13/06 | (2006.01) |
| C12N 9/00 | (2006.01) |
| C12N 9/10 | (2006.01) |
| C12N 1/20 | (2006.01) |
| C12N 15/00 | (2006.01) |
| C07H 21/04 | (2006.01) |

(52) U.S. Cl. ........................ 435/116; 435/183; 435/193; 435/252.3; 435/320.1; 536/23.2

(58) Field of Classification Search ........................ None
See application file for complete search history.

(56) References Cited

U.S. PATENT DOCUMENTS

| | | | |
|---|---|---|---|
| 3,755,081 | A | 8/1973 | Yamade |
| 4,782,021 | A | 11/1988 | Ishiwata et al. |
| 5,346,828 | A | 9/1994 | Stirling et al. |
| 6,037,154 | A | 3/2000 | Suga et al. |
| 2005/0214912 | A1 | 9/2005 | Nozaki et al. |
| 2006/0035345 | A1 | 2/2006 | Nakamatsu et al. |
| 2006/0183190 | A1 | 8/2006 | Suzuki et al. |
| 2006/0263861 | A1 | 11/2006 | Nozaki et al. |
| 2007/0026504 | A1 | 2/2007 | Suzuki et al. |

FOREIGN PATENT DOCUMENTS

| | | |
|---|---|---|
| JP | 6181788 | 7/1994 |
| JP | 7327688 | 12/1995 |
| JP | 11-266881 | 10/1999 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*

Avenoza, A., et al., "Enantioselective synthesis of (S)- and (R)-α-methylserines: application to the synthesis of (S)-and (R)-N-Boc-N,O-isopropylidene-α-methylserinals," Tetrahedron: Assymetry 2001;12:949-957.

Colson, P-J, et al., "Asymmetric Synthesis of α-Alkyl-α-amino Acids from Chromium-Carbene-Complex-Derived β-Lactams," J. Org. Chem. 1993;58:5918-5924.

Ito, Y., et al., "Asymmetric Aldol Reaction of α-Isocyanocarboxylates With Paraformaldehyde Catalyzed by Chiral Ferrocenylphosphine-Gold(I) Complexes: Catalytic Asymmetric Synthesis of α-Alkylserines," Tetrahedron Lett. 1988;29(2):235-238.

Nájera, C., et al., "Asymmetric Synthesis of α-Methyl α-Amino Acids through Diastereoselective Alkylation under Mild Reaction Conditions of an Iminic Alanine Template with a 1,2,3,6-Tetrahydro-2-pyrazinone Structure," Eur. J. Org. Chem. 2000:2809-2820.

(Continued)

*Primary Examiner*—Christian L Fronda
(74) *Attorney, Agent, or Firm*—Shelly Guest Cermak; Cermak Nakajima LLP

(57) ABSTRACT

The present invention provides a new method for producing serine derivatives and their optically-activated derivatives in a convenient manner. In the presence of an enzyme, an L-α-amino acid of formula (I):

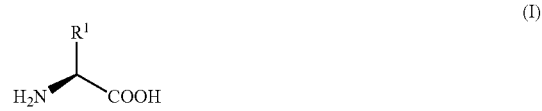

(in the formula (I), $R^1$ is a hydrocarbon group)
is reacted with an aldehyde of formula (II):

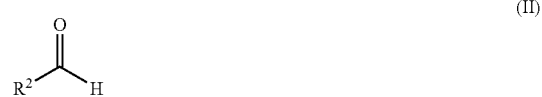

(in the formula (II), $R^2$ is a hydrocarbon)
to produce an L-serine derivative of formula (III).

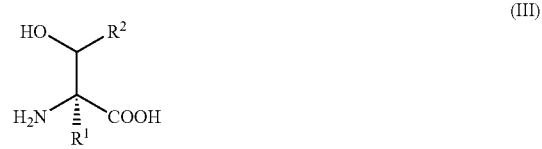

11 Claims, 1 Drawing Sheet

OTHER PUBLICATIONS

Seebach, D., et al., "Stereoselective Alkylation at C($\alpha$) of Serine, Glyceric Acid, Threonine, and Tartaric Acid Involving Heterocyclic Enolates with Exocyclic Double Bonds," Helvetica Chimica Acta 1987;70:1194-1216.

Tanaka, Y., et al., "Cultural Conditions for Microbial Conversion of Glycine into L-Serine in the Presence of Tribasic Magnesium Phosphate," J. Ferment. Technol. 1980;58(5):417-422.

Wilson, E. M., et al., "Metabolism of $\alpha$-Methylserine," J. Biol. Chem. 1962;237(10):3171-3179.

Wipf, P., et al., "A New Synthesis of $\alpha$-Methylserine by Nucleophilic Ring-Opening of N-Sulfonyl Arizidines," Tetrahedron Lett. 1995;36(21):3639-3642.

Nozaki, H., et al., "Purification and Gene Cloning of $\alpha$-Methylserine Aldolase from *Raistonia* sp. Strain AJ110405 and Application of the Enzyme in the Synthesis of $\alpha$-Methyl-L-Serine," Appl. Environmen. Microbiol. 2008;74(24):7596-7599.

Nozaki, H., et al., "Gene Cloning of $\alpha$-Methylserine Aldolase from *Variovorar paradoxus* and Purification and Characterization of the Recombinant Enzyme," Biosci. Biotechnol. Biochem. 2008;72(10):2580-2588.

Supplementary European Search Report for EP Patent App. No. 06756354.4 (Dec. 29, 2009).

U.S. Appl. No. 11/782,260, filed Jul. 24, 2007, Suzuki et al.

U.S. Appl. No. 11/924,760, filed Oct. 26, 2007, Nakamatsu et al.

\* cited by examiner

METHOD OF PRODUCING L-SERINE DERIVATIVE AND ENZYME USED THEREFORE

This application claims priority under 35 U.S.C. §119 to Japanese Patent Application No. 2005-148660, filed May 20, 2005, and is a continuation under 35 U.S.C. §120 of PCT Patent Application No. PCT/JP2006/309949, filed May 18, 2006, both of which are incorporated by reference. The Sequence Listing filed electronically herewith is also hereby incorporated by reference in its entirety (File Name: US-352_Seq_List_Copy__1; File Size: 64 KB; Date Created: Nov. 20, 2007).

BACKGROUND OF THE INVENTION

1. Field of the Invention

The present invention relates to a method for producing β-hydroxy-α-L-amino acid and in particular, to a method for producing an L-serine derivative with a novel enzyme.

2. Brief Description of the Related Art

Derivatives of the amino acid serine and amino acids having optical activity in the a position are typically used as intermediates in the production of pharmaceuticals. Examples of methods for producing optically active α-alkyl serine derivatives, which have two different substituents in the α position, and salts thereof, include the following methods:

1) asymmetric alkylation of an optically active oxazolidine compound obtained from the optically active serine derivative and pivalaldehyde (Helvetica Chimica Acta, 1987, 70, 1194-1216);

2) asymmetric aldol reaction of α-isocyano carboxylic acid ester and paraformaldehyde with an optically active metal catalyst (Tetrahedron Letters, 1988, 29, 235-238);

3) asymmetric alkylation of optically active β-lactam compounds obtained from an optically active oxazolidine chromium carbene complex and an oxazine compound (Journal of Organic Chemistry, 1993, 58, 5918-5924);

4) asymmetric ring-opening reaction of an optically active aziridine compound (Tetrahedron Letters, 1995, 36, 3639-3642)

5) asymmetric alkylation of an optically active pyrazinone compound obtained from an optically active valine derivative and an optically active alanine derivative (European Journal of Organic Chemistry, 2000, 2809-2820); and 6) Sharpless asymmetric dihydroxylation of a 2-methyl-2-propenoic acid derivative followed by introduction of the resulting optically active diol compound into an optically active azido compound for reduction (Tetrahedron Asymmetry, 2001, 12, 949-957).

α-Methyl-L-serine is a promising substance which may be used as an intermediate in the production of a medicament. In one of the known methods for producing α-methyl-L-serine by means of an enzymatic reaction, D-alanine and 5,10-methylenetetrahydrofolic acid are used as the materials, and 2-methyl serine hydroxymethyl transferase (EC 2.1.2.7) is used as the enzyme (Wilson et al., J. Biol. Chem. 237 3171-3179).

SUMMARY OF THE INVENTION

As mentioned above, many studies have been conducted on a wide variety of methods for producing optically active amino acids. However, there are many kinds of optically active amino acids and serine derivatives. A simpler method or an effective and low-cost method for producing optically active amino acids and serine derivatives is desired. An aspect of the present invention is to provide a novel simpler method for producing the serine derivatives and optically active substance thereof, as well as enzymes useful in such methods.

The inventors of the present invention have developed a novel method for producing serine derivatives, and have discovered a new protein. This protein catalyzes the reaction of an L-amino acid and a predetermined aldehyde. In addition, the inventors discovered that this protein could be used to conveniently produce serine derivatives, and also selectively produce an L-serine derivative having optical activity. Therefore, a reaction system in which the amino acid and formaldehyde were directly reacted in the absence of 5,10-methylenetetrahydro folic acid, was established. This type of reaction system has not been found before. The present invention is based on the knowledge of these discoveries by the inventors. The present invention provides a method for producing an L-serine derivative and enzymes used in the method, as mentioned below.

It is an aspect of the present invention to provide a method for producing a L-serine derivative of formula (III):

comprising:
reacting L-α-amino acid of formula (I):

with aldehyde of formula (II):

in the presence of an enzyme,
wherein $R^1$ is selected from the group consisting of an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, and these groups may be either linear or branched and may have a substituent, and
wherein $R^2$ is selected from a group of a hydrogen, an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, and these groups may be either linear or branched and may have a substituent.

It is a further aspect of the present invention to provide the method for producing the L-serine derivative as described above, wherein said enzyme is derived from a microorganism belonging to a genus selected from the group consisting of *Ralstonia, Variovorax, Bosea* and *Silicibacter*.

It is a further aspect of the present invention to provide the method for producing the L-serine derivative as described above, wherein said enzyme is a protein selected from a group consisting of:

(A) a protein comprising the amino acid sequence of SEQ ID No: 5;

(B) a protein comprising an amino acid sequence which has variation of one or a small number of amino acid(s) in the amino acid sequence of SEQ ID NO: 5, wherein said variation is selected from the group consisting of substitution, deletion, insertion, addition and inversion, and wherein said protein has an activity of catalyzing the reaction to form said L-serine derivative of formula (III);

(C) a protein comprising the amino acid sequence of SEQ ID NO: 9;

(D) a protein comprising an amino acid sequence which has variation of one or a small number of amino acid(s) in the amino acid sequence of SEQ ID NO: 9, wherein said variation is selected from the group consisting of substitution, deletion, insertion, addition and inversion, and wherein said protein has an activity of catalyzing the reaction to form said L-serine derivative of formula (III);

(E) a protein comprising an amino acid sequence of SEQ ID NO: 15;

(F) a protein comprising an amino acid sequence which has variation of one or a small number of amino acid(s) in the amino acid sequence of SEQ ID NO: 15, wherein said variation is selected from the group consisting of substitution, deletion, insertion, addition and inversion, and wherein said protein has an activity of catalyzing the reaction to form said L-serine derivative of formula (III);

(G) a protein comprising the amino acid sequence of SEQ ID NO: 19;

(H) a protein comprising an amino acid sequence which has variation of one or a small number of amino acid(s) in the amino acid sequence of SEQ ID NO: 19, wherein said variation is selected from the group consisting of substitution, deletion, insertion, addition and inversion, and wherein said protein has an activity of catalyzing the reaction to form said L-serine derivative of formula (III);

(I) a protein comprising the amino acid sequence of SEQ ID NO: 23;

(J) a protein comprising an amino acid sequence which has variation of one or a small number of amino acid(s) in the amino acid sequence of SEQ ID NO: 23, wherein said variation is selected from the group consisting of substitution, deletion, insertion, addition and inversion, and wherein said protein has an activity of catalyzing the reaction to form said L-serine derivative of formula (III);

(K) a protein comprising the amino acid sequence of SEQ ID NO: 30; and (L) a protein comprising an amino acid sequence which has variation of one or a small number of amino acid(s) in the amino acid sequence of SEQ ID NO: 30, wherein said variation is selected from the group consisting of substitution, deletion, insertion, addition and inversion, and wherein said protein has an activity of catalyzing the reaction to form said L-serine derivative of formula (III).

It is a further aspect of the present invention to provide the method for producing the L-serine derivative as described above, wherein said L-α-amino acid is L-α-alanine and said L-serine derivative is α-methyl-L-serine.

It is a further aspect of the present invention to provide the method for producing the L-serine derivative as described above, wherein said L-α-amino acid is L-2-amino-n-butyric acid and said L-serine derivative is α-ethyl-L-serine.

It is a further aspect of the present invention to provide the method for producing the L-serine derivative as described above, wherein said L-α-amino acid is L-α-alanine and said L-serine derivative is α-methyl-L-threonine.

It is a further aspect of the present invention to provide a protein derived from a microorganism belonging to a genus selected from the group consisting of *Ralstonia, Variovorax, Bosea*, and *Silicibacter*, wherein said protein is able to catalyze a reaction of an L-α-amino acid of formula (I):

with an aldehyde of formula (II)

to produce a L-serine derivative of formula (III):

wherein $R^1$ is selected from the group of an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, and these groups may be either linear or branched and may have a substituent, and wherein $R^2$ is selected from a group of a hydrogen, an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, and these groups may be either linear or branched and may have a substituent.

It is a further aspect of the present invention to provide a protein which is able to catalyze a reaction of an L-α-amino acid of formula (I):

with an aldehyde of formula (II)

(II)

to produce a L-serine derivative of formula (III):

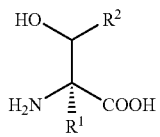
(III)

wherein R$^1$ is selected from the group consisting of an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, and these groups may be either linear or branched and may have a substituent, and wherein R$^2$ is selected from the group consisting of a hydrogen, an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, and these groups may be either linear or branched and may have a substituent, and wherein said protein is selected from the group consisting of:

(A) a protein comprising the amino acid sequence of SEQ ID No: 5;

(B) a protein comprising an amino acid sequence which has variation of one or a small number of amino acid(s) in the amino acid sequence of SEQ ID NO: 5, wherein said variation is selected from the group consisting of substitution, deletion, insertion, addition and inversion, and wherein said protein has an activity of catalyzing the reaction to form said L-serine derivative of formula (III);

(C) a protein comprising the amino acid sequence of SEQ ID NO: 9;

(D) a protein comprising an amino acid sequence which has variation of one or a small number of amino acid(s) in the amino acid sequence of SEQ ID NO: 9, wherein said variation is selected from the group consisting of substitution, deletion, insertion, addition and inversion, and wherein said protein has an activity of catalyzing the reaction to form said L-serine derivative of formula (III);

(E) a protein comprising an amino acid sequence of SEQ ID NO: 15;

(F) a protein comprising an amino acid sequence which has variation of one or a small number of amino acid(s) in the amino acid sequence of SEQ ID NO: 15, wherein said variation is selected from the group consisting of substitution, deletion, insertion, addition and inversion, and wherein said protein has an activity of catalyzing the reaction to form L-serine derivative of formula (III);

(G) a protein comprising the amino acid sequence of SEQ ID NO: 19;

(H) a protein comprising an amino acid sequence which has variation of one or a small number of amino acid(s) in the amino acid sequence of SEQ ID NO: 19, wherein said variation is selected from the group consisting of substitution, deletion, insertion, addition and inversion, and wherein said protein has an activity of catalyzing the reaction to form said L-serine derivative of formula (III);

(I) a protein comprising the amino acid sequence of SEQ ID NO: 23;

(J) a protein comprising an amino acid sequence which has variation of one or a small number of amino acid(s) in the amino acid sequence of SEQ ID NO: 23, wherein said variation is selected from the group consisting of substitution, deletion, insertion, addition and inversion, and wherein said protein an activity of catalyzing the reaction to form said L-serine derivative of formula (III);

(K) a protein comprising the amino acid sequence of SEQ ID NO: 30; and (L) a protein comprising an amino acid sequence which has variation of one or a small number of amino acid(s) in the amino acid sequence of SEQ ID NO: 30, wherein said variation is selected from the group consisting of substitution, deletion, insertion, addition and inversion, and wherein said protein has an activity of catalyzing the reaction to form said L-serine derivative of formula (III).

It is a further aspect of the present invention to provide a polynucleotide encoding a protein as described above.

It is a further aspect of the present invention to provide a polynucleotide selected from the group consisting of:

(a) a polynucleotide comprising the nucleotide sequence of SEQ ID NO: 4;

(b) a polynucleotide which hybridizes with a polynucleotide having a nucleotide sequence complementary to that of SEQ ID NO: 4 under stringent conditions, and which encodes a protein having an activity of catalyzing the reaction of an L-α-amino acid of formula (I) with an aldehyde of formula (II) to produce an L-serine derivative of formula (III);

(c) a polynucleotide comprising the nucleotide sequence of SEQ ID NO: 8;

(d) a polynucleotide which hybridizes with a polynucleotide having a nucleotide sequence complementary to that of SEQ ID NO: 8 under stringent conditions, and which encodes a protein having an activity of catalyzing the reaction of an L-α-amino acid of formula (I) with an aldehyde of formula (II) to produce an L-serine derivative of formula (III);

(e) a polynucleotide comprising the nucleotide sequence of SEQ ID NO: 14;

(f) a polynucleotide which hybridizes with a polynucleotide having a nucleotide sequence complementary to that of SEQ ID NO: 14 under stringent conditions, and which encodes a protein having an activity of catalyzing a reaction of an L-α-amino acid of formula (I) with an aldehyde of formula (II) to produce an L-serine derivative of formula (III);

(g) a polynucleotide comprising the nucleotide sequence of SEQ ID NO: 18;

(h) a polynucleotide which hybridizes with a polynucleotide having a nucleotide sequence complementary to that of SEQ ID NO: 18 under stringent conditions, and which encodes a protein having an activity of catalyzing the reaction of an L-α-amino acid of formula (I) with an aldehyde of formula (II) to produce an L-serine derivative of formula (III);

(i) a polynucleotide comprising the nucleotide sequence of SEQ ID NO: 22;

(j) a polynucleotide which hybridizes with a polynucleotide having a nucleotide sequence complementary to that of SEQ ID NO: 22 under stringent conditions, and which encodes a protein having an activity of catalyzing the reaction of an L-α-amino acid of formula (I) with an aldehyde of formula (II) to produce an L-serine derivative of formula (III);

(k) a polynucleotide comprising the nucleotide sequence of SEQ ID NO: 29; and (l) a polynucleotide which hybridizes with a polynucleotide having a nucleotide sequence complementary to that of SEQ ID NO: 29 under stringent conditions, and which encodes a protein having an activity of catalyzing the reaction of an L-α-amino acid of formula (I) with an aldehyde of formula (II) to produce an L-serine derivative of formula (III); and wherein formula (I) is:

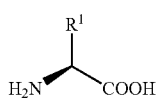
(I)

wherein $R^1$ of formula (I) is selected from the group consisting of an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, and these groups may be either linear or branched and may have a substituent;

wherein said formula (II) is:

(II)

wherein $R^2$ of formula (II) is selected from the group consisting of a hydrogen, an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, and these groups may be either linear or branched and may have a substituent;

wherein said formula (III) is:

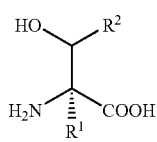
(III)

It is a further aspect of the present invention to provide a recombinant polynucleotide comprising said polynucleotide as described above.

It is a further aspect of the present invention to provide a transformant having said polynucleotide as described above.

The present invention allows L-serine derivatives to be produced by a simple method. Moreover, the present invention allows L-amino acids, such as the L-serine derivative having an optical activity, to be selectively produced, which provides an effective method for producing these types of L-amino acids.

DESCRIPTION OF THE PREFERRED EMBODIMENTS

Figure 1:
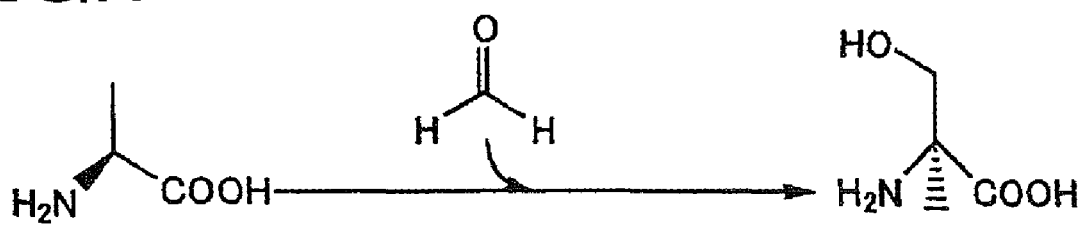
FIG. 1 is a scheme showing the reaction system.

Hereinafter, embodiments according to the present invention are described with reference to the best mode of carrying out the invention.

Various types of genetic engineering approaches and methods are described in many standard experimental manuals, such as Molecular Cloning: A Laboratory Manual, $3^{rd}$ edition, Cold Spring Harbor press (2001/01/15), *Saibo Kogaku Handbook* (Cellular Engineering Handbook), Toshio KUOKI et al., Yodosya (1992), and Shin Idenshi Kogaku Handbook (New Gene Engineering Handbook), $3^{rd}$ edition, Matsumura et al., Yodosya (1999), and by reference to these, any person skilled in the art may easily use these methods. An enzyme is a protein which is able to catalyze a chemical reaction.

To produce an L-serine derivative, an L-α-amino acid of formula (I) is reacted with an aldehyde of formula (II).

The alkyl group of $R^1$ with 1 to 6 carbons includes, but is not limited to, a methyl group, an ethyl group, a n-propyl group, an isopropyl group, a n-butyl group, an isobutyl group, a sec-butyl group, a tert-butyl group, a n-pentyl group, an isopentyl group, a neo-pentyl group, a n-hexyl group, and an isohexyl group.

The aryl group of $R^1$ with 6 to 14 carbons includes, but is not limited to, a phenyl group, a tolyl group, a xylyl group, a biphenylyl group, a naphthyl group, an antolyl group, and a phenantolyl group.

The cycloalkyl group of $R^1$ with 3 to 10 carbons includes, but is not limited to, a cyclopropyl group, a cyclobutyl group, a cyclopentyl group, a cyclohexyl group, a cycloheptenyl group, a cyclooctanyl group, a cyclononenyl group, and a cyclodecenyl group.

The aralkyl group of $R^1$ with 7 to 19 carbons includes, but is not limited to, phenylalkyl groups such as a benzyl group, a benzhydryl group, a phenethyl group, and a trityl group, a cinnamyl group, a stylyl group, and a naphthylalkyl group.

The alkoxyalkyl group of $R^1$ with 2 to 11 carbons includes, but is not limited to an alkyl group with 1 to 10 carbons which has a substituent selected from the group consisting of a methoxy group, an ethoxy group, a propoxy group, an isopropoxy group, a butoxy group, a pentyloxy group, a phenoxy group, a heptoxy group, an octoxy group, a nonanoxy group, a decanoxy group, and an undecoxy group.

$R^1$ may also be a group which has a carbon skeleton containing a hetero atom in any of the aforementioned hydrocarbons. Examples of the hetero atom include, but are not limited to, an oxygen atom, a nitrogen atom, and a sulfur atom.

When $R^1$ is a hydrocarbon group containing a hetero atom in its carbon skeleton, it may include a heterocycle-containing hydrocarbon group. The heterocycle-containing hydrocarbon group is a cyclic hydrocarbon group, wherein the cyclic moiety contains the hetero atom. Examples of the heterocyclic hydrocarbon group include, but are not limited to, a heteroaryl group with or without aromaticity and may be either a monocyclic or polycyclic group. Specific examples of the heterocyclic hydrocarbon group include, but are not limited to, a furilic group, a thienyl group, a pyridyl group, a piperidyl group, a piperidino group, a morpholino group, an indolyl group, an imidazolyl group, and an alkyl group substituted with any of these heterocyclic groups.

In addition, $R^1$ may also be a hydrocarbon group which has a carbon skeleton containing a unsaturated carbon-carbon bond in any of the aforementioned groups.

In addition, the aforementioned $R^1$ may be linear or branched. Moreover, $R^1$ may be the aforementioned hydrocarbon group which is partially substituted with the following group or to which the following group is partially added: one or more groups which may include a halogen atom, an alkyl group with up to 3 carbons, an alkoxyl group with up to 3 carbons, a keto group (=O), a hydroxyl group (—OH), a thiol group (—SH), an amino group (—NH$_2$), an amido group (—CONH$_2$), an imino group (=NH), and a hydrazino group (—NHNH$_2$).

Examples of the L-α-amino acid of formula (I) include, but are not limited to, alanine, valine, leucine, isoleucine, serine, threonine, cysteine, methionine, asparagine, glutamine, phenylalanine, tyrosine, tryptophan, aspartic acid, glutamic acid, lysine, arginine, histidine, and 2-amino-n-butyric acid. All of these are of the L-α-type, preferably, alanine and 2-amino-n-butyric acid, and more preferably, alanine.

$R^2$ of formula (II) may be specifically described as follows. $R^2$ may be hydrogen.

The alkyl group of $R^2$ with 1 to 6 carbons includes, but is not limited to, a methyl group, an ethyl group, a n-propyl group, an isopropyl group, a n-butyl group, an isobutyl group, a sec-butyl group, a tert-butyl group, a n-pentyl group, an isopentyl group, a neo-pentyl group, n-hexyl group, and an isohexyl group.

The aryl group of $R^2$ with 6 to 14 carbons includes, but is not limited to, a phenyl group, a tolyl group, a xylyl group, a biphenylyl group, a naphthyl group, an antolyl group, and a phenantolyl group.

When $R^2$ is a cycloalkyl group with 3 to 10 carbons, specific examples include, but are not limited to, a cyclopropyl group, a cyclobutyl group, a cyclopentyl group, a cyclohexyl group, a cycloheptenyl group, a cyclooctanyl group, a cyclononenyl group, and a cyclodecenyl group.

The aralkyl group of $R^2$ with 7 to 19 carbons includes, but is not limited to, phenylalkyl groups such as a benzyl group, a benzhydryl group, a phenethyl group, and a trityl group, a cinnamyl group, a stylyl group, and a naphthylalkyl group.

The alkoxyalkyl group of $R^2$ with 2 to 11 carbons includes, but is not limited to an alkyl group with 1 to 10 carbons which has a substituent of a methoxy group, an ethoxy group, a propoxy group, an isopropoxy group, a butoxy group, a pentyloxy group, a phenoxy group, a heptoxy group, an octoxy group, a nonanoxy group, a decanoxy group, or an undecoxy group.

$R^2$ may also be a group which has a carbon skeleton containing a hetero atom in any of aforementioned hydrocarbon groups. The examples of the hetero atom include, but are not limited to, an oxygen atom, a nitrogen atom, and a sulfur atom.

When $R^2$ is a hydrocarbon group containing a hetero atom in its carbon skeleton, it may include a heterocycle-containing hydrocarbon group. The heterocycle-containing hydrocarbon group is a cyclic hydrocarbon group, wherein a cyclic moiety contains the hetero atom. Examples of the heterocycle-containing hydrocarbon group includes, but is not limited to, a heteroaryl group with or without aromaticity and may be either monocyclic or polycyclic group. Specific examples of the heterocyclic hydrocarbon group include, but are not limited to, a furilic group, a thienyl group, a pyridyl group, a piperidyl group, a piperidino group, a morpholino group, an indolyl group, an imidazolyl group, and an alkyl group substituted by any of these heterocyclic groups.

In addition, $R^2$ may also be a hydrocarbon group which has a carbon skeleton containing an unsaturated carbon-carbon bond in any of the aforementioned groups.

In addition, the aforementioned $R^2$ may be linear or branched. Moreover, $R^2$ may be the aforementioned hydrocarbon group which is partially substituted with the following group or to which the following group is partially added: one or more groups selected from a group of a halogen atom, an alkyl group with up to 3 carbons, an alkoxyl group with up to 3 carbons, a keto group (=O), a hydroxyl group (—OH), a thiol group (—SH), an amino group (—NH$_2$), an amido group (—CONH$_2$), an imino group (=NH), a hydrazino group (—NHNH$_2$).

Examples of compounds of formula (II) may preferably include formaldehyde and acetaldehyde.

$R^1$ and $R^2$ of formula (III) are the same as $R^1$ and $R^2$ of formula (I) and (II), respectively. According to a specific combination of $R^1$ and $R^2$, the product may be an optically-inactive stereoisomer (mesoisomer). The method of the present invention is a method for producing an amino acid having an optical activity; therefore, the present invention does not include a combination of $R^1$ and $R^2$ which result in the production of the mesoisomer. For example, α-hydroxymethyl-serine is not an L-serine derivative; therefore, the combination of serine as a compound of formula (I) and formaldehyde as a compound of formula (II) is not included in the method for producing the L-serine derivative of the present invention.

The method of the present invention for producing the L-serine derivative involves a process of preferentially producing the L-serine derivative by the reaction with an enzyme. Herein, the phrase "preferentially producing the L-serine derivative" means that the ratio of the L-serine derivative is higher than the ratio of a D-serine derivative among the serine derivatives to be produced, and the ratio is preferably 70% or more, more preferably 80% or more, and further preferably 90% or more. In this case, the ratio of the L-serine derivative among the L-serine derivatives is calculated by the formula:

[L-serine derivative]/([D-serine derivative]+[L-serine derivative])*100.

One preferred embodiment of the method of the present invention includes a reaction system, in which α-methyl-L-serine is produced through the reaction of L-α-alanine and formaldehyde. FIG. 1 shows a specific example of the reaction system. The reaction system, in which formaldehyde is reacted directly with the L-amino acid without involving a compound such as 5,10-methylentetrahydro folic acid to produce the L-serine derivative, has not been known at all. According to the method of the present invention, the L-serine derivative may be produced in a simpler reaction system. In the case of using formaldehyde, it is preferable that a small amount of formaldehyde is added sequentially in the reaction system. The sequential addition of formaldehyde may suppress the generation of byproducts.

Another preferable embodiment of the present invention may include reaction systems in which α-ethyl-L-serine is produced through the reaction of L-2-amino-n-butyric acid and formaldehyde; and α-methyl-L-threonine is produced through the reaction of L-α-alanine and acetaldehyde.

A reaction temperature is preferably 10 to 60° C. and more preferably 20 to 40° C. The pH value for the reaction system is preferably 4 to 10 and more preferably 6 to 8.

An example of the method of isolating an L-serine derivative from the resulting solution of the aforementioned enzymatic reaction is as follows. Dissolved proteins are flocculated by lowering the pH with thermal sterilization, and then microbes and proteins are removed from the solution by means such as centrifugation, filtration, and ultra filtration (UF). Because the resulting solution includes inorganic salts, the solution is desalted to avoid precipitation of those salts during crystallization. Applicable methods may include any method such as nanofiltration (NF), electrodialysis, and ion exchange using a resin.

After the aforementioned desalting, when necessary, the solution is concentrated. Then, the L-serine derivative begins to crystallize; however, due to the crystals' fine and highly solvable properties, it is often difficult to isolate. Furthermore, the ratio of the recovered crystals cannot be allowed to be high, and the high viscosity makes handling difficult.

Therefore, crystallization by adding a poor solvent is preferably conducted after the solution is preliminarily concentrated to some extent, when necessary. For example, the preliminary concentrating may be continued until crystals begin to precipitate. Preferable examples of the poor solvent include lower alcohols and acetone, which are water soluble. Continuing with cooling crystallization after the crystallization with the poor solvent may also help to improve the crystallization ratio. The resulting slurry is isolated and the wetting cake thereof is dried to obtain crystals of the L-serine derivative.

According to the method of the present invention, an aldehyde of formula (II) is reacted with the L-α-amino acid in the presence of a predetermined enzyme. The enzyme capable of catalyzing the reaction may be obtained from a microorganism belonging to a genus such as *Ralstonia, Variovorax, Bosea*, and *Silicibacter*. More specific examples of the microorganism may include *Ralstonia* sp., *Variovorax paradoxus*, *Bosea* sp. and *Silicibacter pomeroyi*; preferably, *Ralstonia* sp. FERM ABP-10607, *Variovorax paradoxus* FERM ABP-10608, *Variovorax paradoxus* NBRC 15149, *Variovorax paradoxus* NBRC 15150, *Bosea* sp. FERM ABP-10609 and *Silicibacter pomeroyi* DSM 15171.

Strains having a FERM or NBRC number assigned are deposited strains as mentioned below; therefore, they are available by referencing the associated number and following the given procedure.

(1) Nomenclature: *Ralstonia* sp. A11 (or, AJ110405)
Deposit Number: FERM ABP-10607
Depositary authority: International Patent Organism Depositary, National Institute of Advanced Industrial Science and Technology
Address: Chuoh No. 6, Higashi 1-1-1, Tsukuba, Ibaraki, Japan
Deposit date: Mar. 8, 2005

(2) Nomenclature: *Variovorax paradoxus* B2-B2 (or, AJ110406 strain)
Deposit Number: FERM ABP-10608
Depositary authority: International Patent Organism Depositary, National Institute of Advanced Industrial Science and Technology
Address: Chuoh No. 6, Higashi 1-1-1, Tsukuba, Ibaraki, Japan
Deposit date: Mar. 8, 2005

(3) Nomenclature: *Variovorax paradoxus* AJ110408
Deposit Number: NBRC15149
Depositary authority: NITE Biological Resource Center
Department of Biotechnology (NBRC), Department of Biotechnology (DOB), National Institute of Technology and Evaluation (NITE)
Address: Kazusa Kamatari 2-5-8, Kisarazu, Chiba, Japan (4) Nomenclature: *Variovorax paradoxus* AJ110409
Deposit Number: NBRC15150
Depositary authority: NITE Biological Resource Center
Department of Biotechnology (NBRC), Department of Biotechnology (DOB), National Institute of Technology and Evaluation (NITE)
Address: Kazusa Kamatari 2-5-8, Kisarazu, Chiba, Japan (5) Nomenclature: *Bosea* sp. B2-R1 (or, AJ110407)
Deposit Number: FERM ABP-10609
Depositary authority: International Patent Organism Depositary, National Institute of Advanced Industrial Science and Technology
Address: Chuoh No. 6, Higashi 1-1-1, Tsukuba, Ibaraki, Japan
Deposit date: Mar. 8, 2005

Other than those strains, *Silicibacter pomeroyi* DSM 15171 is accessible to the public at Deusche Sammulung von Mikroorganismen und Zellkulturen GmbH (Address: Mascheroder Weg 1b, 38124 Braunschweig, GERMANY), and at the American Type Culture Collection (Contact: P.O. Box 1549, Manassas, Va. 20108, U.S.A.), with the reference number ATCC700808.

Tables 1-1 and 1-2 describe the mycological characteristics of *Ralstonia* sp. All strain (or, AJ110405, Deposit NO: FERM ABP-10607).

TABLE 1-1

| *Ralstonia* sp. A11 | |
|---|---|
| 1. Morphological characteristics | |
| Culture conditions | Nutrient agar (Oxoid, Hampshire, England) culture medium, 30° C. |
| Cell morphology | Short *bacillus* (0.6 × 0.8 μm) |
| Cell polymorphism | − |
| Motility (flagellar immobility) | − |
| Spore (sporal site) | − |
| 2. Culture characteristics | |
| Culture conditions | Nutrient agar (Oxoid, Hampshire, England) culture medium, 30° C. |
| Color | Pale yellow |
| Luster | + |
| Color development | − |
| Culture conditions | Nutrient broth (Oxoid, Hampshire, England) culture medium, 30° C. |
| Surface growth | − |
| Cloudiness of culture medium | + |
| Culture condition | Gelatin stick culture 30° C. |
| Growth condition | + |
| Gelatin liquification[1] | − |
| Culture condition[2] | Litmus milk 30° C. |
| Coagulation | − |
| Liquification | − |
| 3. Physiological characteristics | |
| Gram stainability[1] | − |
| Nitrate reduction[3] | − |
| denitrification[3] | + |
| MR test[2] | − |
| VP test[3] | − |
| Indole production[3] | − |
| Production of hydrogen sulfide[3] | − |
| Starch hydrolysis[2] | − |
| Use of citric acid[2] (Koser) | + |
| (Christensen) | + |
| Use of inorganic nitrogen resource[2] Nitrate | + |
| Ammonium salt | + |
| Urease activity[3] | − |

TABLE 1-1-continued

| Ralstonia sp. A11 | | |
|---|---|---|
| Catalase[2] | | + |
| Oxidase[2] | | + |
| Growth range; pH | 6 | + |
| | 8 | + |
| | 9 | +w |
| Growth range; temperature (° C.) | 25 | + |
| | 30 | + |
| | 37 | +w |
| | 45 | − |
| Anaerobic growth | | − |
| O—F test (acidic/fermented)[2] | | −/− |

TABLE 1-2

| 4. Acid production/gas generation from saccharide[2] | | | |
|---|---|---|---|
| L-arabinose | −/− | D-xylose | −/− |
| D-glucose | −/− | D-mannose | −/− |
| D-fractose | −/− | D-galactose | −/− |
| maltose | −/− | sucrose | −/− |
| lactose | −/− | Trehalose | −/− |
| D-sorbitol | −/− | D-mannitol | −/− |
| inositol | −/− | Glycerin | −/− |
| 5. Other physiological characteristics[2] | | | |
| β-galactosidase activity | − | | |
| arginine dihydrolase activity | − | | |
| lysine decarboxylase activity | − | | |
| tryptophan deaminase activity | − | | |
| Gelatinase activity | − | | |

+: positive,
−: negative,
w: weakly reacted

Tables 2-1 and 2-2 describe the mycological characteristics of *Variovorax paradoxus* B2-B2 (AJ110406 strain, Deposit NO: FERM ABP-10608).

TABLE 2-1

| Variovorax paradoxus B2-B2 | |
|---|---|
| 1. Morphological characteristics | |
| Culture conditions | Nutrient agar (Oxoid, Hampshire, England) culture medium, 30° C. |
| Cell morphology | (0.6-07 × 1.5-2.0 μm) |
| Cell polymorphism | − |
| Motility (flagellar immobility) | + |
| Spore (sporal site) | − |
| 2. Culture characteristics | |
| Culture conditions | Nutrient agar (Oxoid, Hampshire, England) culture medium, 30° C. |
| Color | Yellow |
| Luster | + |
| Color development | + |
| Culture condition | Nutrient broth (Oxoid, Hampshire, England) culture medium, 30° C. |
| Surface growth | − |
| Cloudiness of culture medium | + |
| Culture conditions | Gelatin stick culture 30° C. |
| Growth conditions | − |
| Gelatin liquification[1] | − |
| Culture conditions[2] | Litmus milk 30° C. |
| Coagulation | − |
| Liquification | − |

TABLE 2-1-continued

| Variovorax paradoxus B2-B2 | | |
|---|---|---|
| 3. Physiological characteristics | | |
| Gram stainability[1] | | − |
| Nitrate reduction[3] | | − |
| denitrification[3] | | + |
| MR test[2] | | − |
| VP test[3] | | − |
| Indole production[3] | | − |
| Production of hydrogen sulfide[3] | | − |
| Starch hydrolysis[2] | | − |
| Use of citric acid[2] | (Koser) | − |
| | (Christensen) | + |
| Use of inorganic nitrogen resource[2] | Nitrate | +w |
| | Ammonium salt | +w |
| Urease activity[3] | | − |
| Catalase[2] | | + |
| Oxidase[2] | | − |
| Growth range; pH | 6 | + |
| | 8 | + |
| | 9 | + |
| Growth range; temperature (° C.) | 25 | + |
| | 30 | + |
| | 37 | +w |
| | 45 | − |
| Anaerobic growth | | + |
| O—F test (acidic/fermented)[2] | | −/− |

TABLE 2-2

| 4. Acid production/gas generation from saccharide[2] | | | |
|---|---|---|---|
| L-arabinose | −/− | D-xylose | −/− |
| D-glucose | −/− | D-mannose | −/− |
| D-fractose | −/− | D-galactose | −/− |
| maltose | −/− | sucrose | −/− |
| lactose | −/− | Trehalose | −/− |
| D-sorbitol | −/− | D-mannitol | −/− |
| inositol | −/− | Glycerin | −/− |
| 5. Other physiological characteristics[2] | | | |
| β-galactosidase activity | − | | |
| arginine dihydrolase activity | − | | |
| lysine decarboxylase activity | − | | |
| tryptophan deaminase activity | − | | |
| Gelatinase activity | − | | |

+: positive,
−: negative,
w: weakly reacted

Tables 3-1 and 3-2 describe the mycological characteristics of *Bosea* sp. B2-R1 strain (AJ110407, Deposit NO: FERM ABP-10609).

TABLE 3-1

| Bosea sp. B2-R1 | |
|---|---|
| 1. Morphological characteristics | |
| Culture conditions | Nutrient agar (Oxoid, Hampshire, England) culture medium, 30° C. |
| Cell morphology | (0.6-07 × 1.5-2.0 μm) |
| Cell polymorphism | − |
| Motility (flagellar immobility) | + |
| Spore (sporal site) | − |
| 2. Culture characteristics | |
| Culture conditions | Nutrient agar (Oxoid, Hampshire, England) culture medium, 30° C. |

TABLE 3-1-continued

Bosea sp. B2-R1

| | |
|---|---|
| Color | Pale yellow |
| Luster | + |
| Color development | − |
| Culture conditions | Nutrient agar (Oxoid, Hampshire, England) culture medium, 30° C. |
| Surface growth | − |
| Cloudiness of culture medium | + |
| Culture conditions | Gelatin stick culture 30° C. |
| Growth conditions | − |
| Gelatin liquification[1] | − |
| Culture conditions[2] | Litmus milk 30° C. |
| Coagulation | − |
| Liquification | − |

3. Physiological characteristics

| | | |
|---|---|---|
| Gram stainability[1] | | − |
| Nitrate reduction[3] | | − |
| denitrification[3] | | − |
| MR test[2] | | − |
| VP test[3] | | − |
| Indole production[3] | | − |
| Production of hydrogen sulfide[3] | | − |
| Starch hydrolysis[2] | | − |
| Use of citric acid[2] | (Koser) | + |
| | (Christensen) | + |
| Use of inorganic nitrogen resource[2] | Nitrate | + |
| | Ammonium salt | +w |
| Urease activity[3] | | − |
| Catalase[2] | | + |
| Oxidase[2] | | + |
| Growth range; pH | 6 | + |
| | 8 | + |
| | 9 | + |
| Growth range; temperature (° C.) | 25 | + |
| | 30 | + |
| | 37 | + |
| | 45 | − |
| Anaerobic growth | | + |
| O—F test (acidic/fermented)[2] | | −/− |

TABLE 3-2

4. Acid production/gas generation from saccharide[2]

| | | | |
|---|---|---|---|
| L-arabinose | −/− | D-xylose | −/− |
| D-glucose | −/− | D-mannose | −/− |
| D-fractose | −/− | D-galactose | −/− |
| maltose | −/− | sucrose | −/− |
| lactose | −/− | Trehalose | −/− |
| D-sorbitol | −/− | D-mannitol | −/− |
| inositol | −/− | Glycerin | −/− |

5. Other physiological characteristics[2]

| | |
|---|---|
| β-galactosidase activity | − |
| arginine dihydrolase activity | − |
| lysine decarboxylase activity | − |
| tryptophan deaminase activity | − |
| Gelatinase activity | − |

+: positive,
−: negative,
w: weakly reacted

References and Kits Used:
1) BARROW, (G. I.) and FELTHAM, (R. K. A): Cowan and Steel's Manual for the Identification of Medical Bacteria. 3$^{rd}$ edition. 1993, Cambridge University Press.
2) Toshikazu SAKAZAKI, Etsuro YOSHIZAKI, and Kanji MIKI: *Shin Saikin-baichi-gaku Kouza PART II* (The Course of Culturing Medium for Microorganism PART II) <2$^{nd}$ edition>, 1988, Kindai Shuppan, Tokyo.
3) Bacteriopexy kit: AP120, NE. (bioMerieux, France:http://www.biomerieux.fr/home_en.htm).

More specifically, examples of the enzymes used in the reaction for producing the L-serine derivative includes the following proteins:

(A) a protein of the amino acid sequence of SEQ ID No: 5;
(B) a protein of an amino acid sequence which has variation of one or a small number of amino acid(s) in the amino acid sequence of SEQ ID NO: 5, wherein said variation is a substitution, deletion, insertion, addition and inversion, and wherein the protein has an activity of catalyzing the reaction to form said L-serine derivative of formula (III);
(C) a protein of the amino acid sequence of SEQ ID NO: 9;
(D) a protein of an amino acid sequence which has variation of one or a small number of amino acid(s) in the amino acid sequence of SEQ ID NO: 9, wherein said variation is a substitution, deletion, insertion, addition and inversion, and wherein the protein has an activity of catalyzing the reaction to form said L-serine derivative of formula (III);
(E) a protein of an amino acid sequence of SEQ ID NO: 15;
(F) a protein of an amino acid sequence which has variation of one or a small number of amino acid(s) in the amino acid sequence of SEQ ID NO: 15, wherein said variation is a substitution, deletion, insertion, addition and inversion, and wherein the protein has an activity of catalyzing the reaction to form said L-serine derivative of formula (III);
(G) a protein of the amino acid sequence of SEQ ID NO: 19;
(H) a protein of an amino acid sequence which has variation of one or a small number of amino acid(s) in the amino acid sequence of SEQ ID NO: 19, wherein said variation is a substitution, deletion, insertion, addition and inversion, and wherein the protein has an activity of catalyzing the reaction to form said L-serine derivative of formula (III);
(I) a protein of the amino acid sequence of SEQ ID NO: 23;
(J) a protein of an amino acid sequence which has variation of one or a small number of amino acid(s) in the amino acid sequence of SEQ ID NO: 23, wherein said variation a substitution, deletion, insertion, addition and inversion, and wherein the protein has an activity of catalyzing the reaction to form said L-serine derivative of formula (III);
(K) a protein of the amino acid sequence of SEQ ID NO: 30; and
(L) a protein of an amino acid sequence which has variation of one or a small number of amino acid(s) in the amino acid sequence of SEQ ID NO: 30, wherein said variation is a substitution, deletion, insertion, addition and inversion, and wherein the protein has an activity of catalyzing the reaction to form said L-serine derivative of formula (III).

Any of the aforementioned proteins may be used to conveniently produce the L-serine derivative. In particular, when L-α-alanine reacts with formaldehyde, only α-methyl-L-serine is substantially produced. The optically active amino acid is therefore efficiently obtained.

The protein having the amino acid sequence of SEQ ID NO: 5 may be isolated from *Ralstonia* sp. FERM ABP-10607. The protein having the amino acid sequence of SEQ ID NO: 9 may be isolated from *Variovorax paradoxus* FERM ABP- 10608. The protein having the amino acid sequence of SEQ ID NO: 15 may be isolated from *Variovorax paradoxus* NBRC15149. The protein having the amino acid sequence of SEQ ID NO: 19 may be isolated from *Variovorax paradoxus* NBRC15150. The protein having the amino acid sequence of SEQ ID NO: 23 may be isolated from *Bosea* sp. FERM ABP-10609. The protein having the amino acid sequence of SEQ ID NO: 30 may be isolated from *Silicibacter pomeroyi* DSM 15171.

The genome sequence of *Silicibacter pomeroyi* DSM 15171 has been disclosed and a part of the sequence of SEQ ID NO: 30 is registered as a serine hydroxymethyltransferase (AAV96754.1). As a result, serine hydroxymethyltransferase (AAV96754.1) which has the registered sequence was expressed in *Eshcerichia coli*, and the desired protein was not detected and the resulting products did not have any serine hydroxymethyltransferase activity. However, as a result of research by the inventors, it was discovered that nine amino acid residues upstream of the registered sequence is necessary for activity of 2-methylserine hydroxymethyltransferase. Therefore, the nine amino acid residues is added upstream of the registered sequence, resulting in the sequence of SEQ ID NO: 30. As a result of expressing the sequence of SEQ ID NO: 30 in *Eshcerichia coli*, it was confirmed that the desired protein was detected, which has 2-methylserine hydroxymethyltransferase activity.

As mentioned above, variant proteins which are substantially the same as the above-mentioned proteins may be used. First, taking the protein of SEQ ID NO: 5 as an example, a protein which is substantially the same as the protein of SEQ ID NO: 5 is also provided. Herein, the term "a small number" indicates a number of amino acids which result in a protein structure which retains substantially the same activity, specifically 1 to 50, preferably 1 to 30, and more preferably 1 to 10, depending on the position of the amino acid residue in the protein structure and the type of amino acid. The amino acid sequence of the variant protein, which has variation of one or a small number of amino acid(s), in which the variation is a substitution, deletion, insertion, addition, and inversion, preferably conserves approximately half or more of the oxygen activity, preferably 80% or more, more preferably 90% or more, and further preferably 95% compared with the protein (A) under the conditions of 30° C., pH 7 to 8.

The variation in amino acids as described in the aforementioned variant protein may be achieved by alternating the nucleotide sequence so that the amino acid which corresponds to the specific site of the gene encoding the protein is substituted, deleted, inserted, or added using, e.g., the site-specific mutagenic method. Alternatively, the polynucleotide having the nucleotide sequence altered as mentioned above may be obtained through known conventional mutation process. The mutation process includes in vitro treatment of the DNA encoding the protein of SEQ ID NO: 5, for example, with hydroxylamine or the like and a method in which the microorganism belonging to genus *Escherichia*, which carries DNA encoding the protein of SEQ ID NO: 5 is treated with UV irradiation or with a mutagenic agent which is commonly used for artificial mutation such as N-methyl-N'-nitro-N-nitrosoguanidine (NTG) and nitrous acid.

The aforementioned variation, such as substitution, deletion, addition, and inversion, also includes naturally-occurring variation such as differences in species and strain of the microorganism. By expressing the DNA having the variation mentioned above in appropriate cells to examine the enzyme activity of the expressed products, the DNA encoding the variant protein may be obtained.

Similar to the relationship between the protein of SEQ ID NO: 5 and its variant protein, each of the proteins of SEQ ID NOs. 9, 15, 19, 23, and 30 may also exist as variant proteins which are substantially the same as defined above for the protein of SEQ ID NO. 5 and its variant.

Examples of the variant proteins which are substantially the same as the proteins of SEQ ID NOs. 9, 15, 19, 23, and 30 include proteins which have an amino acid sequence with homology of preferably 70% or more, more preferably 80% or more, and further preferably 90% or more, with respect to each of the proteins. In the present specification, the homology of the amino acid sequence was obtained by calculating a Marching count which indicates the percentage over the full-length of the ORF of the encoded polypeptide, using GENETYX software Ver7.0.9 (Genetics) with Unit Size to Compare=2, or by an equivalent calculation method.

The present invention provides polynucleotides encoding the aforementioned proteins. Due to codon degeneration, an amino acid sequence may be defined by more than one nucleotide sequence. That is, the polynucleotide of the present invention includes a polynucleotide having the nucleotide sequences encoding the aforementioned proteins of SEQ ID NOs. 9, 15, 19, 23, and 30, and their variants.

Specifically, examples of the polynucleotides of the present invention include, but are not limited to, the following polynucleotides:

(a) a polynucleotide of a nucleotide sequence of SEQ ID NO: 4;

(c) a polynucleotide of a nucleotide sequence of SEQ ID NO: 8;

(e) a polynucleotide of a nucleotide sequence of SEQ ID NO: 14;

(g) a polynucleotide of a nucleotide sequence of SEQ ID NO: 18;

(i) a polynucleotide of a nucleotide sequence of SEQ ID NO: 22; and (k) a polynucleotide of a nucleotide sequence of SEQ ID NO: 29.

The polynucleotide of SEQ ID NO. 4, encoding the protein of SEQ ID NO. 5, may be isolated from the *Ralstonia* sp. FERM ABP-10607. The polynucleotide of SEQ ID NO. 8, encoding the protein of SEQ ID NO. 9, may be isolated from the *Variovorax paradoxus* FERM ABP-10608. The polynucleotide of SEQ ID NO. 14, encoding the protein of SEQ ID NO. 15, may be isolated from the *Variovorax paradoxus* NBRC15149. The polynucleotide of SEQ ID NO. 18, encoding the protein of SEQ ID NO. 19, may be isolated from the *Variovorax paradoxus* NBRC15150. The polynucleotide of SEQ ID NO. 22, encoding the protein of SEQ ID NO. 23, may be isolated from the *Bosea* sp. FERM ABP-10609. The polynucleotide of SEQ ID NO. 29, encoding the protein of SEQ ID NO. 30, may be isolated from the *Silicibacter pomeroyi* DSM 15171.

Taking the polynucleotide of SEQ ID NO. 4 as an example, a method for isolating polynucleotides is described. The DNA having the nucleotide sequence listed in the sequence of SEQ ID NO. 4 may be obtained from a chromosomal DNA or a DNA library of *Ralstonia* sp. by PCR (polymerase chain reaction, refer to White, T. J. et al; Trends Genet., 5, 185 (1989)) or hybridization. A primer which can be used in PCR may be designed based on, for example, an internal amino acid sequence of the purified protein having an activity of catalyzing the reaction involved in the method of the present invention. Alternatively, the primer or a probe for hybridization may be designed based on the nucleotide sequence of SEQ ID NO: 4 or may be isolated using a probe. A combination of a primer having a sequence corresponding to a 5' non-translated region, and a sequence corresponding to a 3' non-translated region, between which is found the coding region, may be used for the primer for PCR. Then, PCR can be used to amplify the full-length of the protein coding region.

The primer may be synthesized in a typical manner, for example, by the phosphoramidite method (refer to Tetrahedron Letters (1981), 22, 1859) using DNA synthesizing equipment Model 380B (Applied Biosystems). The PCR process may be conducted using, for example, Gene Amp PCR System 9600 (PERKIN ELMER) and TaKaRa LA PCR in vitro Cloning Kit (TaKaRa Bio), according to the method specified by the suppliers or manufacturers.

Variant polynucleotides which are substantially the same as the aforementioned polynucleotides of SEQ ID NOs. 4, 8, 14, 18, 22, and 29 are also included in the present invention.

A variant polynucleotide of SEQ ID NO. 4 includes a polynucleotide which hybridizes with a polynucleotide having a nucleotide sequence complementary to that of SEQ ID NO: 4 under stringent conditions, and which encodes a protein having an activity of catalyzing the reaction of an L-α-amino acid of formula (I) with an aldehyde of formula (II) to produce an L-serine derivative of formula (III);

A variant polynucleotide of SEQ ID NO. 8 includes a polynucleotide which hybridizes with a polynucleotide having a nucleotide sequence complementary to that of SEQ ID NO: 8 under stringent conditions, and which encodes a protein having an activity of catalyzing the reaction of an L-α-amino acid of formula (I) with an aldehyde of formula (II) to produce an L-serine derivative of formula (III);

A variant polynucleotide of SEQ ID NO. 14 includes a polynucleotide which hybridizes with a polynucleotide having a nucleotide sequence complementary to that of SEQ ID NO: 14 under stringent conditions, and which encodes a protein having an activity of catalyzing the reaction of an L-α-amino acid of formula (I) with an aldehyde of formula (II) to produce an L-serine derivative of formula (III);

A variant polynucleotide of SEQ ID NO. 18 includes a polynucleotide which hybridizes with a polynucleotide having a nucleotide sequence complementary to that of SEQ ID NO: 18 under stringent conditions, and which encodes a protein having an activity of catalyzing the reaction of an L-α-amino acid of formula (I) with an aldehyde of formula (II) to produce an L-serine derivative of formula (III);

A variant polynucleotide of SEQ ID NO. 22 includes a polynucleotide which hybridizes with a polynucleotide having a nucleotide sequence complementary to that of SEQ ID NO: 18 under stringent conditions, and which encodes a protein having an activity of catalyzing the reaction of an L-α-amino acid formula (I) with an aldehyde of formula (II) to produce an L-serine derivative of formula (III); and A variant polynucleotide of SEQ ID NO. 29 includes a polynucleotide which hybridizes with a polynucleotide having a nucleotide sequence complementary to that of SEQ ID NO: 29 under stringent conditions, and which encodes a protein having an activity of catalyzing the reaction of an L-α-amino acid formula (I) with an aldehyde of formula (II) to produce an L-serine derivative of formula (III).

A probe, for example, may be used to hybridize the polynucleotides as described above. In each case, the probe may be prepared in a typical manner based on the nucleotide sequences of SEQ ID Nos: 4, 8, 14, 18, 22, and 29. The objective polynucleotide may be isolated using the probe to hybridize in the usual manner. The DNA probe, for example, may be prepared by amplifying the nucleotide sequences cloned into a plasmid or a phage vector, cutting out the desired nucleotide sequence with a restriction enzyme, and then extracting the nucleotide sequence. The portion to be cut out may be adjusted according to the objective DNA. Once the aforementioned polynucleotide, which is substantially the same as any other nucleotide, has been detected, the polynucleotide may be amplified in a usual manner, such as PCR.

The "stringent conditions" indicate conditions under which a so-called specific hybrid is formed but a nonspecific hybrid is not formed. Although it is difficult to clearly define the condition in terms of numerical values, an example of such conditions may be those under which the DNAs having high homology, for example, 70% or more, more preferably 80% or more, further preferably 90% or more, and still further preferably 95% or more, are hybridized while the DNAs having lower homology are not hybridized. The homology (%) of the nucleotide sequences is represented by numeric values obtained by percentage calculation over the full-length of the ORF of each gene (including a stop codon) using GENETYX software Ver7.0.9 (Genetics) with Unit Size to Compare=6, pick up location=1. As another example, stringent conditions may be those of ordinary washing conditions in Southern hybridization, under which the DNAs are hybridized at 60° C. and salt concentration of 1×SSC, 0.1% SDS, and preferably 0.1×SSC, 0.1% SDS. The genes which hybridize under such conditions include, but are not limited to, a gene containing a stop codon or a gene encoding a non-active protein due to a mutation in the DNA sequence encoding the activity center region. However, these may be easily screened out by inserting the obtained genes in a commercially-available expression vector, expressing the genes in an appropriate host, and determining the enzyme activity of the expressed product by a method described herein.

As mentioned above, desirably, the aforementioned variant polynucleotide of SEQ ID NO. 4 conserves approximately half or more of catalytic activity, preferably 80% or more, and more preferably 90% or more compared with the protein having the amino acid sequence encoded by the nucleotide sequence of SEQ ID NO: 4 under the conditions of 30° C., pH 8.0. Likewise, the aforementioned relationship is applicable to the aforementioned variant polynucleotide of SEQ ID NO. 8 in connection with the protein of SEQ ID NO. 9; to the aforementioned variant polynucleotide of SEQ ID NO. 14 in connection with the protein of SEQ ID NO. 15; to the aforementioned variant polynucleotide of SEQ ID NO. 18 in connection with the protein of SEQ ID NO. 19; to the aforementioned variant polynucleotide of SEQ ID NO. 22 in connection with the protein of SEQ ID NO. 23; and to the aforementioned variant polynucleotide of SEQ ID NO. 29 in connection with the protein of SEQ ID NO. 30.

According to the method of the present invention, any form of the enzyme may be used as long as it is capable of catalyzing the aforementioned reaction in the reaction system. Examples of the specific forms thereof include a cultured product of an enzyme-producing microorganism, cells of the microorganism separated from the cultured product, and a processed cell product. The cultured product of the microorganism is a product obtained by culturing the microorganism. More specifically, the cultured product may include a product such as a mixture containing the cells of the microorganisms, the cultivation medium used for culturing the microorganism, and the substances produced by the cultured microorganism. The cells of the microorganisms may be washed before using. The processed cell product may be disrupted, lysed, and/or freeze-dried. Also, a crude-purified protein that is collected from the processed cells, and a purified protein that is further purified may also be used. As for the purified proteins, a partially-purified protein which is obtained by a variety of purification methods may be used. Alternatively, a protein which is fixed by a covalent bond method, an adsorption method, or an entrapment method may be used. Depending on the chosen microorganism, a the cells may be lysed during cultivation. In this case, the supernatant of the cultivation medium may also be used as the enzyme-containing substance.

Next, the method for producing the proteins of the present invention, and the method for preparing the recombinants and transformants used in producing the proteins will be described hereinbelow using the aforementioned protein of SEQ ID NO. 5 as an example. These methods of the present invention are also applicable to other proteins.

The transformant which expresses the aforementioned protein of SEQ ID NO. 5 may be prepared using a previously prepared recombinant polynucleotide which contains the polynucleotide having any of the aforementioned nucleotide sequences incorporated therein. The transformant which expresses the aforementioned protein of SEQ ID NO. 5 may be obtained by, for example, preparing a recombinant DNA containing a DNA having the nucleotide sequence of SEQ ID NO: 4, and then introducing the resulting DNA into an appropriate host. Examples of the host for expressing the protein include a variety of prokaryotic cells, including microorganisms belonging to genus *Escherichia* such as *Escherichia coli*, microorganisms belonging to genus *Corynebacterium*, *Bacillus subtilis*, and a variety of eukaryotic cells including *Saccharomyces cerevisiae*, *Pichia stipitis*, and *Aspergillus oryzae*. When a host is chosen which is easily handled without any expensive components for cultivation, L-serine derivatives may be easily produced on a large scale.

The recombinant DNA for introducing the DNA of SEQ ID NO. 4 into a host may be prepared by inserting the DNA into a vector suitable for the type of the host, so that the inserted DNA can express the protein encoded thereby. If the native promoter to the gene encoding the aforementioned enzyme derived from microorganisms such as *Ralstonia* sp., *Variovorax paradoxus*, and *Bosea* sp. is capable of functioning in the host cell, this promoter may be used to express the protein. Alternatively, if necessary, other promoters which function in the host may be linked to the DNA of SEQ ID NO: 4, for example, so that the proteins are expressed under the control of the promoter.

The method for introducing the recombinant DNA into the host cell includes the D. M. Morrison method (Methods in Enzymology 68, 326 (1979)) and a method for increasing the permeability of the DNA by treating the recipient host cells with calcium chloride (Mandel, M. and Higa, A., J. Mol. Biol., 53, 159 (1970)).

When the objective proteins are produced on a large-scale using recombinant DNA technology, the association of the proteins to form protein inclusion bodies within the host transformant, is also for a preferred method for carrying out the present invention. The advantages of this expression production method is the protection of the objective protein from digestion from proteases in the microbial cells, and easy purification of the objective protein by disruption of the microbial cells followed by centrifugation. To obtain the active protein from the protein inclusion body, a series of manipulations such as solubilization and activity regeneration is required, and thus, the manipulations are more complicated than those used when directly producing the active protein. However, when a protein which affects microbial cell growth is produced on a large scale in the microbial cells, the effects thereof may be avoided by accumulating the protein as an inactive inclusion body in the microbial cells.

Examples of the methods for producing the objective protein on a large scale as an inclusion body includes methods of expressing the objective protein alone under the control of a strong promoter, as well as methods of expressing the objective protein as a fusion protein with a protein known to be expressed in a large amount.

As the host to be transformed, any strain commonly used to express heterogenes may be used. Suitable examples thereof include the *Escherichia coli* JM109, DH5α, HB101, and BL21(DE3) strains, which are subspecies of the *Escherichia coli* K12 strain. The method for transforming the host and the method for selecting the transformants are described in Molecular Cloning: A Laboratory Manual, 3rd edition, Cold Spring Harbor press (2001/01/15). An example of the method for preparing the transformed *Escherichia coli* and producing a predetermined enzyme using the transformed *E. coli* will be specifically described hereinbelow.

As the promoter for expressing the DNA encoding the protein having catalytic activity used for the present invention, the promoters typically used for producing xenogenic proteins in *E. coli* may be used, and examples thereof may include strong promoters such as T7 promoter, lac promoter, trp promoter, trc promoter, tac promoter, and PR promoter and PL promoter, T5 promoter of lambda phage. As the vector, pUC19, pUC18, pBR322, pHSG299, pHSG298, pHSG399, pHSG398, RSF1010, PACYC177, pACYC184, pMW119, pMW118, pMW219, pMW218, pQE30, and derivatives thereof may be used. Other vectors of phage DNA may also be used. In addition, expression vectors which contain a promoter and can express the inserted DNA sequence may also be used.

In order to produce the protein in the form of a fusion protein inclusion body, a fusion protein gene is prepared by linking a gene encoding the second protein, preferably a hydrophilic peptide, to the upstream or downstream of the aforementioned protein. Such a gene encoding another protein may be those which increase the amount of the accumulated fusion protein and enhance the solubility of the fusion protein after denaturation and regeneration. Examples of candidates thereof may include the T7 gene 10, β-galactosidase gene, dehydrofolic acid reductase gene, interferon γ gene, interleukin-2 gene and prochymosin gene.

Such a gene may be ligated to the gene encoding the protein so that reading frames of codons are matched. This may be achieved by ligating at an appropriate restriction enzyme site or using a synthetic DNA having an appropriate sequence.

In some cases, it is preferable to ligate a terminator, i.e. the transcription termination sequence, downstream of the fusion protein gene in order to increase the production amount. Examples of this terminator may include T7 terminator, fd phage terminator, T4 terminator, tetracycline resistant gene terminator, and *E. coli* trpA gene terminator.

The vector for introducing the gene encoding the protein having catalytic activity or the fusion protein thereof into *E. coli* is preferably a multicopy vector. Examples thereof include plasmids having a replication origin derived from ColE1, such as pUC based plasmids, pBR322 based plasmids or derivatives thereof. As used herein, the term "derivative" means the plasmid modified by the substitution, deletion, insertion, addition and/or inversion of bases. "Modified" referred to herein includes modification by mutagenesis with a mutagen or UV irradiation, and natural mutation.

In order to select the transformants, it is preferable to employ a vector having a marker such as an ampicillin resistant gene. As such a plasmid, expression vectors having a strong promoter are commercially available (pUC series: Takara Bio Co., Ltd., pPROK series and pKK233-2: Clontech, etc.).

The DNA fragment containing the promoter, the gene encoding the protein having the objective activity or the fusion protein of the objective protein with the other protein, and in some cases the terminator, are ligated sequentially, and then ligated to the vector DNA to obtain a recombinant DNA.

The resulting recombinant DNA is used to transform *Escherichia coli*, and then the transformed *Escherichia coli* is cultured, so to express and produce the predetermined protein or its fused protein.

In the case of expressing the fusion protein, the fusion protein may be cleaved to obtain the objective protein using a restriction protease which recognizes a sequence not present in the objective protein, such as blood coagulation factor Xa, kallikrein.

As production media, media such as M9-casamino acid medium and LB medium which are typically used for cultivation of *E. coli* may be used. The conditions for cultivation and a production induction may be appropriately selected depending on types of the marker and the promoter of the vector and the host used.

The following methods are available for recovering the objective protein or the fusion protein containing the objective protein. If the objective protein or the fusion protein thereof is solubilized in the microbial cells, the cells may be collected and then disrupted or lysed to thereby obtain a crude enzyme solution. If necessary, the crude solution may be purified using techniques such as ordinary precipitation, filtration and column chromatography, to obtain the purified objective protein or the fusion protein. In this case, the purification may be performed using an antibody against the objective protein or the fusion protein. When the protein inclusion body is formed, it may be solubilized with a denaturant, and then the denaturant may be removed by dialysis or the like to obtain the objective protein.

EXAMPLES

The present invention will be described in more detail with reference to the following non-limiting examples.

Example 1

Detection of 2-Methyl Serine Hydroxylmethyl Transferase Activity

In a Nutrient Broth agar medium (Difco), the microorganisms listed in Table 4 were cultured at 30° C. for 24 hours. A platinum loopful of the resulting cells were inoculated into 3 ml of Nutrient Broth liquid medium and then cultured at 30° C. for 24 hours, with 120 reciprocations/minute. 0.15 ml of the resulting culture was inoculated into 3 ml of Nutrient Broth liquid medium containing 0.2% α-methyl-DL-serine and cultured at 30° C. for 24 hours at 120 reciprocations/minute.

After cultivation, the cells were centrifuged and then washed twice with an equal volume of 50 mM potassium phosphate buffer (pH 7.4) containing 0.1 mM pyridoxal phosphate. 50 mM potassium phosphate buffer (pH 7.4) containing 0.1 mM pyridoxal phosphate was used to prepare a total amount (0.3 ml) of cell suspension, and then the suspension was ultrasonically disrupted at 4° C. The supernatant obtained by centrifugation (16,000 g, 10 min.) was dialyzed with 50 mM potassium phosphate buffer (pH 7.4) containing 0.1 mM pyridoxal phosphate to obtain a cell-free extracted solution.

0.05 ml of the cell-free extracted solution was added to a reaction mixture of 50 mM potassium phosphate buffer (pH 7.4), 10 mM α-methyl-DL-serine, 0.1 mM pyridoxal phosphate, and 1 mM magnesium sulfate, and then a total amount (0.1 ml) of mixture was reacted at 30° C. for 10 minutes. The reaction was stopped by mixing 0.1 ml of alkaline agent (5N-potassium hydroxide) supplied with the Formaldehyde Kit-Test Wako (Wako). Subsequently, the formaldehyde detection reaction was executed by reference to the manual supplied with the kit to measure absorbance at 550 nm (E11). As a control, another reaction was performed in the same way as above, except that α-methyl-DL-serine was replaced with water in the aforementioned solution, and the absorbance (E10) of the resulting mixture was measured.

The change in adsorption specific to α-methyl-DL-serine was calculated (EΔ1=E11−E10). The results are shown in Table 4. As the results shows, 2-methyl serine hydroxymethyl transferase activity was confirmed.

TABLE 4

| Strain | EΔ1 |
| --- | --- |
| *Ralstonia* sp. A11 | 0.70 |
| *Variovorax paradoxus* B2-B2 | 0.86 |
| *Bosea* sp. B2-R1 | 0.42 |

Example 2

Purification of 2-Methyl Serine Hydroxymethyl Transferase Derived from and Native to the *Ralstonia* sp. A11 (AJ110405) Strain (1) Preparation of the Cell-Free Extracted Solution Cells of *Ralstonia* species were cultured in the Nutrient Broth agar medium (Difco) at 30° C. for 25.5 hours. The cultured cells were inoculated into 50 ml of Nutrient Broth liquid medium in a 500 ml Sakaguchi flask, and cultured at 30° C. for 21 hours, 120 reciprocation/minute. The resulting culture was inoculated into 2 L of liquid medium containing 0.2% α-methyl-DL-serine, 0.17% Yeast Nitrogen Base w/o amino acid and ammonium sulfate (pH 7.0). 100 ml each of the mixture was dispensed into 500 ml Sakaguchi flasks, and then cultured at 30° C. for 24 hours, 120 reciprocation/minute. The resulting cells were collected by centrifugation (8,000 g, 10 minutes) and washed twice with 25 mM Tris-HCl buffer (pH 8.0) containing 0.02 mM pyridoxal phosphate, and then 50 ml of cell suspension was prepared. The cells were ultrasonically disrupted and centrifuged (18,000 g, 10 minutes), and the resulting supernatant was ultra-centrifuged (200,000 g, 30 minutes). The resulting supernatant was dialyzed using the same buffer, thus obtaining a cell-free extracted solution.

(2) Anion-Exchange Chromatography

The cell-free extracted solution obtained in the aforementioned (1) was applied in ResourceQ columns (Amersham Biosciences), which had been previously equilibrated with 25 mM tris-HCl buffer (pH8.0) containing 0.02 mM pyridoxal phosphate, and the enzyme was eluted by a linear concentration gradient of 0-1M sodium chloride. This process was conducted three times by dividing the cell-free extracted solution into three aliquots.

(3) Hydrophobic Interaction Chromatography

Active fractions of the enzyme obtained in the aforementioned (2) were dialyzed in 25 mM tris-HCl buffer (pH7.4) containing 0.02 mM pyridoxal phosphate (hereinafter, simply referred to as the buffer I), and mixed with the buffer I containing an equivalent amount of 2M ammonium sulfate, and then applied to Phenyl-Sepharose columns (Amersham Biosciences) which had been previously equilibrated with the buffer I containing 1M ammonium sulfate. Then, the enzyme was eluted by the linear concentration gradient of 1-0M ammonium sulfate.

(4) Hydroxyapatite Column Chromatography

The active fractions obtained in the aforementioned (3) were dialyzed with 2.5 mM potassium phosphate buffer (pH 7.0) containing 0.02 mM pyridoxal phosphate, and then applied in the CellulofineHAp columns (SEIKAGAKU Corp.) which had been previously equilibrated with the same buffer. The enzyme was eluted in 2.5-500 mM potassium phosphate buffer (pH7.0).

The active fractions of the enzyme having 0.72 U/mg of relative activity, which were obtained in this manner, were electrophoresed with SDS-polyacrylamide, and the gel was stained with Coomassie brilliant blue staining fluid. A homogeneous band appeared at a position of approximately 47,000 of molecular weight.

Example 3

Determination of the Amino Acid Sequence and the Encoding Nucleotide Sequence of 2-Methyl Serine Hydroxymethyl Transferase Derived from and Native to the *Ralstonia* sp. A11 (AJ110405) Strain 100 pmol of purified enzyme, which had been prepared in Example 2, was electrophoresed in SDS-polyacrylamide, transcribed on a PVDF membrane, and then put in a protein sequencer to determine 30 amino acids (SEQ ID NO: 1).

Second, 5 µg of genomic DNA derived from the *Ralstonia* sp. AJ110405 was cleaved with SalI (75 U), and then ligated to SalI cassettes in line with the method described in the manual supplied with the TaKaRa LA PCR in vitro Cloning Kit. Using the ligated mixture as a template, PCR (94° C.: 30 sec., 47° C.: 2 min., 72° C.: 1 min., 30 cycles) was performed with a combination of a cassette primer C1 and a primer ALD_RV_S1 (SEQ ID NO: 2). Subsequently, using the PCR reaction mixture as a template, the second PCR (94° C.: 30 sec., 55° C.: 2 min., 72° C.: 1 min., 30 cycles) was performed with a cassette primer C2 and a primer ALD_RV_S2 (SEQ ID NO: 3). Approximately 0.7 kb-length fragments which were amplified, were ligated to pGEM-Teasy (Promega) and used to transform *Escherichia coli* JM109.

Defining the nucleotide sequence of approximately 0.7 kb of fragments, the nucleotide sequence encoding the N terminal amino acid sequence of the objective protein was detected. Using approximately 0.3 kb-length gene fragments obtained by treating the plasmid with EcoRI/SphI as a probe, chromosomal DNAs were subject to Southern analysis after treatment with various types of restriction enzymes. When the chromosome DNAs were treated with SphI, a positive signal was confirmed in an approximately 2.4 kb region.

Subsequently, the chromosomal DNAs were treated with SphI, and then electrophoresed in an agarose gel, to purify the approximately 2.5 kb fragment. The fragment was then ligated to the pUC18 SphI site. Using this reaction mixture, *Escherichia coli* JM109 was transformed to create a library. The aforementioned probe was used to perform colony hybridization to obtain positive colonies. A plasmid was extracted from the positive colonies. Using the resulting plasmid as pSKA04098, the nucleotide sequences of the inserted sequence were determined. An ORF (SEQ ID NO. 4) encoding 438 amino acids was found.

Example 4

Expression of 2-Methyl Serine Hydroxymethyl Transferase Gene Derived from and Native to the *Ralstonia* Sp. A11 (AJ110405) in *Escherichia coli*

Using pSKA04098 as a template, PCR was performed with the primer Ral_Eco (SEQ ID NO: 6) and the primer Ral_ter_Pst (SEQ ID NO: 7) to amplify a 1.3 kb region of 2-methyl serine hydroxymethyl transferase. The amplified sequence was treated with EcoRI/PstI, and then ligated to pUC18 which had been previously treated with EcoRI/PstI, to transform *Escherichia coli* JM109. The transformant having plasmid (pRal2) containing the objective gene fragments was obtained and designated JM109/pRal2.

JM109/pRal2 was pre-cultured in the LB culture medium containing 100 mg/l ampicillin at 37° C. for 16 hours. 0.15 ml of pre-cultured solution was inoculated into 3 ml LB culture medium containing 100 mg/l ampicillin and cultured at 37° C. One hour after the onset, IPTG was added so that the final concentration thereof reached 1 mM, and then the mixture was further cultured for four hours. The resulting cells were collected by centrifugation and washed with the 50 mM phosphoric acid buffer (pH 7.4) containing 0.1 mM pyridoxal phosphate.

A cell suspension was then prepared using 0.3 mL of the same buffer. The cells were ultrasonically disrupted and centrifuged (18,000 g, 10 min., 4° C.) to obtain a supernatant as a cell-free extracted solution. 2-methyl serine hydroxymethyl transferase activity was measured in the supernatant. The measured value was 0.03 U/mg. On the other hand, in the case of using a cell-free extracted solution obtained by the aforementioned method using the transformant JM109/pUC18, which is a transformant obtained by introducing pUC18 into JM109, the measured activity thereof was below the detection limit.

Example 5

Production of α-Methyl-L-Serine with 2-Methyl Serine Hydroxymethyl Transferase Derived from *Ralstonia* Sp. A11 (AJ110405)

50 µl of purified enzyme solution prepared in Example 2 was added to a solution of 100 mM formaldehyde, 100 mM L-alanine, 0.1 mM pyridoxal phosphate, and 100 mM phosphoric acid buffer (pH7.4). The reaction was performed at 30° C. for 20 hours. As formaldehyde, the highest quality of formaldehyde liquid product [code No.: 16223-55] from Nakarai Tesk was used. After the reaction, 100 µl of 1 mM aqueous copper sulfate and 50 µl of water were added to 50 µl of the reaction mixture, and then HPLC analysis was performed using Sumichiral OA-6100 (Sumitomo Kagaku Analysis Center) (mobile phase: 0.5 mM aqueous copper sulfate, column temperature: 30° C., flow rate: 1 ml/min., detection: UV215 nm). The result showed that 27.5 mM α-methyl-L-serine was produced but no peak attributed to α-methyl-D-serine was detected. As a reference standard, α-methyl-L-serine [Code NO: 29001-2500], α-methyl-D-serine [Code NO: 29002-2500] from Acros Organics were used.

Example 6

Production of α-Methyl-L-Serine Using the 2-Methyl Serine Hydroxymethyl Transferase Gene-Expressed *Escherichia coli* Derived from *Ralstonia* Sp. A11 (AJ110405)

JM109/pRal2 was cultured in LB medium containing 100 mg/l at 30° C. for 24 hours, and further cultured in the LB medium containing 100 mg/l and 0.5 mM IPTG at 34° C. for 16 hours. The cells obtained in 400 ml of the cultured medium were collected by centrifugation, and then washed with the 100 mM phosphoric acid buffer (pH7.4) containing 0.1 mM pyridoxal phosphate. The resulting cells were suspended in 100 ml of reaction mixture (300 mM L-alanine, 0.1 mM pyridoxal phosphate, 100 mM phosphoric acid buffer (pH7.4)). 50.5 ml of 600 mM aqueous formaldehyde was added to the reaction mixture at 30° C. over 24 hours while stirring. As formaldehyde, the highest quality of formaldehyde liquid product [code No.: 16223-55] from Nakarai Tesk was used. After the adding process, 50 μl of 1 mM aqueous copper sulfate and 100 μl of water were added to 50 μl of the reaction mixture, and HPLC analysis was performed using Sumichiral OA-6100 (Sumitomo Kagaku Analysis Center) (mobile phase: 0.5 mM aqueous copper sulfate, column temperature: 30° C., flow rate: 1 ml/min., detection: UV215 nm). The result showed that 27.0 mmol α-methyl-L-serine was produced but no peak attributable to α-methyl-D-serine was detected.

Example 7

Acquisition of 2-Methyl Serine Hydroxymethyl Transferase Gene Derived from *Variovorax paradoxus* B2-B2 (AJ110406)

In line with the same manner described in Example 3, an ORF domain derived from *Ralstonia* sp. AJ110405 was amplified by PCR. Using the resulting PCR product as a probe, genomic DNA of *Variovorax paradoxus* B2-B2 was subject to Southern analysis after treatment with PstI. A positive signal was found in a region of approximately 2 kb length.

Subsequently, the genomic DNA of *Variovorax paradoxus* B2-B2 was treated with PstI and electrophoresed in an agarose gel. Approximately 2 kb of fragments were purified and ligated to the pUC118 PstI site. Using this reaction mixture, *Escherichia coli* JM109 was transformed to create a library. The aforementioned probe was used to hybridize colonies to collect positive colonies. A plasmid was extracted from the positive colonies. Using the resulting plasmid as pUCB2-B2, the nucleotide sequence of the inserted sequence was determined. The presence of an ORF of 441 amino acids (SEQ ID NO. 8) was confirmed.

Subsequently, using pTV118N (Takara Bio) as a template, primers pTV118N_Nde (SEQ ID NO. 10) and pTV118N_Ndec (SEQ ID NO: 11) were used to obtain pTV118Nd using Quikchange site directed mutagenesis kit (Promega). The amplified fragment of 1.2 kb was obtained by PCR with the primers B2-B2_Nde (SEQ ID NO: 12) and B2-B2_ter_Pst (SEQ ID NO. 13) using pUCB2-B2 as a template. The resulting fragment was treated with NdeI/PstI and inserted into pTV118Nd NdeI/PstI site, which was designated pTVVHMT01. Using this plasmid, *Escherichia coli* JM109 was transformed. The transformant was designated JM109/pTVVHMT01.

JM109/pTVVHMT01 was pre-cultured in LB medium containing 100 mg/l ampicillin and 0.11 mM IPTG at 37° C. for 16 hours. The resulting cells were collected by centrifugation and washed with 50 mM phosphoric acid buffer (pH 7.4) containing 0.1 mM pyridoxal phosphate, and then a cell suspension was prepared with the same buffer. The cells were ultrasonically disrupted and centrifuged (18,000 g, 10 min., 4° C.) to obtain a supernatant as a cell-free extracted solution. 2-methyl serine hydroxymethyl transferase activity was measured in the supernatant. Generated formaldehyde was determined after reaction in the reaction mixture containing 50 mM Tris-HCl buffer (pH8.5), 10 mM α-methyl-L-serine, and 0.1 mM pyridoxal phosphate at a reaction temperature 30° C. The measured value was 9 mU/mg. On the other hand, when using a cell-free extracted solution obtained in line with the aforementioned method using the transformant JM109/pTV118Nd, which is a transformant obtained by introducing pTV118Nd into JM109, the measured activity thereof was below the detection limit.

Example 8

Acquisition of 2-Methyl Serine Hydroxymethyl Transferase Genes Derived from the *Variovorax paradoxus* NBRC15149

In line with the same manner described in Example 3, an ORF domain derived from *Ralstonia* sp. AJ110405 was amplified by PCR. Using the resulting PCR product as a probe, genomic DNA of *Variovorax paradoxus* NBRC 15149 was subjected to Southern analysis after treatment with PstI. A positive signal was found in a 2 kb-length region.

Subsequently, the genomic DNA of *Variovorax paradoxus* NBRC 15149 was treated with PstI and electrophoresed in an agarose gel. Approximately 2 kb of fragments were purified and ligated to the pUC118 PstI site. Using this reaction mixture, *Escherichia coli* JM109 was transformed to create a library. The aforementioned probe was used to hybridize colonies to collect positive colonies. A plasmid was extracted from the positive colonies. Using the resulting plasmid as pUC15149, the nucleotide sequence of the inserted sequence was determined. The presence of an ORF of 440 amino acids (SEQ ID NO: 14) was confirmed. Using pUC15149 as a template, PCR was performed with primers 15149_Nde (SEQ ID NO: 16) and 15149_ter_Pst (SEQ ID NO: 17). An amplified fragment of 1.2 kb was obtained by PCR. The resulting fragment was treated with NdeI/PstI, and inserted into the pTV118Nd NdeI/PstI site, which was designated pTVVHMT02. Using this plasmid, *Escherichia coli* JM109 was transformed. The transformant was designated JM109/pTVVHMT02.

JM109/pTVVHMT02 was pre-cultured in LB medium containing 100 mg/l ampicillin and 0.1 mM IPTG at 37° C. for 16 hours. The resulting cells were collected by centrifugation and washed with 50 mM phosphoric acid buffer (pH7.4) containing 0.1 mM pyridoxal phosphate, and then a cell suspension was prepared with the same buffer. The cells were ultrasonically disrupted and centrifuged (18,000 g, 10 min., 4° C.) to obtain a supernatant as a cell-free extracted solution. 2-methyl serine hydroxymethyl transferase activity was measured in the supernatant. The measured value was 13 mU/mg.

Example 9

Acquisition of 2-Methyl Serine Hydroxymethyl Transferase Genes Derived from the *Variovorax paradoxus* NBRC15150 Strain In accordance with the same manner described in Example 3, an ORF domain derived from *Ralstonia* sp. AJ110405 was amplified by PCR. Using the resulting PCR product as a probe, genomic DNA of *Variovorax paradoxus* NBRC 15150 was subject to Southern analysis after treatment with PstI. A positive signal was found in a 2 kb-length region.

Subsequently, the genomic DNA of *Variovorax paradoxus* NBRC 15150 was treated with PstI and electrophoresed in the agarose gel. Approximately 2 kb of fragments were purified and ligated to the pUC118 PstI site. Using this reaction mixture, *Escherichia coli* JM109 was transformed to create a library. The aforementioned probe was used to hybridize colonies to collect positive colonies. A plasmid was extracted from the positive colonies. Using the resulting plasmid as pUC15150, the nucleotide sequence of the inserted sequence was determined. The presence of an ORF of 440 amino acids (SEQ ID NO: 18) was confirmed. Using pUC15150 as a template, PCR was performed with primers 15150_Nde (SEQ ID NO: 20) and 15150_ter_Pst (SEQ ID NO: 21). The amplified fragment of 1.2 kb was obtained by PCR. The resulting fragment was treated with NdeI/PstI, and inserted into the pTV118Nd NdeI/PstI site, which was designated pTVVHMT03. Using this plasmid, *Escherichia coli* JM109 was transformed. The transformant was designated JM109/pTVVHMT03.

JM109/pTVVHMT03 was pre-cultured in the LB medium containing 100 mg/l ampicillin and 0.1 mM IPTG at 37° C. for 16 hours. The resulting cells were collected by centrifugation and washed with 50 mM phosphoric acid buffer (pH7.4) containing 0.1 mM pyridoxal phosphate, and then a cell suspension was prepared with the same buffer. The cells were ultrasonically disrupted and centrifuged (18,000 g, 10 min., 4° C.) to obtain a supernatant as a cell-free extracted solution. 2-methyl serine hydroxymethyl transferase activity was measured in the supernatant. The measured value was 36 mU/mg.

Example 10

Acquisition of 2-Methyl Serine Hydroxymethyl Transferase Genes Derived from the *Bosea* sp. B2-R1 (AJ110407) Strain In line with the same manner described in Example 3, an OFR domain derived from *Ralstonia* sp. AJ110405 was amplified by PCR. Using the resulting PCR product as a probe, genomic DNA of *Bosea* sp. B2-R1 was subject to Southern analysis after treatment with PstI. A positive signal was found in a 5 kb-length region.

Subsequently, the genomic DNA of the *Bosea* sp. B2-R1 strain was treated with PstI and electrophoresed in an agarose gel. Approximately 5 kb of fragments were purified and ligated to the pUC118 PstI site. Using this reaction mixture, *Escherichia coli* JM109 was transformed to create a library. The aforementioned probe was used to hybridize colonies to collect positive colonies. A plasmid was extracted from the positive colonies. Using the resulting plasmid as pUCB2-R1, the nucleotide sequence of the insertion was determined. The presence of an ORF of 440 amino acids (SEQ ID NO: 22) was confirmed. Using pUCB2-R1 as a template, PCR was performed with primers B2-R1_Psh (SEQ ID NO: 24) and B2-R1_ter_Pst (SEQ ID NO: 25). An amplified fragment of 1.2 kb was obtained by PCR. The resulting fragments were treated with PshBI/PstI, and inserted into the pTV118 NdeI/PstI site, which was designated pTVBHMT. Using this plasmid, *Escherichia coli* JM109 was transformed. The transformant was designated JM109/pTVBHMT. Using pUCB2-R1 as a template, PCR was performed with primers B2-R1_Eco (SEQ ID NO: 26) and B2-R1_ter_Pst (SEQ ID NO: 25). The amplified fragment of 1.2 kb was obtained by PCR. The resulting fragment was treated with EcoRI/PstI, and inserted into pUC18 EcoRI/PstI site, which was designated pUCB-HMT. Using this plasmid, *Escherichia coli* JM109 was transformed. The transformant was designated JM109/pUCB-HMT.

JM109/pTVBHMT was pre-cultured in LB medium containing 100 mg/l ampicillin and 0.1 mM IPTG at 37° C. for 16 hours. The resulting cells were collected by centrifugation and washed with 50 mM phosphoric acid buffer (pH7.4) containing 0.1 mM pyridoxal phosphate, and then a cell suspension was prepared with the same buffer. The cells were ultrasonically disrupted and centrifuged (18,000 g, 10 min., 4° C.) to obtain a supernatant as a cell-free extracted solution. 2-methyl serine hydroxymethyl transferase activity was measured in the supernatant. The measured value was 95 mU/mg. JM109/pUCBHMT was pre-cultured in LB medium containing 100 mg/l ampicillin and 0.1 mM IPTG at 37° C. for 16 hours. The resulting cells were collected by centrifugation and washed with 50 mM phosphoric acid buffer (pH 7.4) containing 0.1 mM pyridoxal phosphate, and then a cell suspension was prepared with the same buffer. The cells were ultrasonically disrupted and centrifuged (18,000 g, 10 min., 4° C.) to obtain a supernatant as a cell-free extracted solution. 2-methyl serine hydroxymethyl transferase activity was measured in the supernatant. The measured value was 318 mU/mg.

In the case of using a cell-free extracted solution obtained in line with the aforementioned method using the JM109/pUC18, the measured activity thereof was below the detection limit.

Example 11

Acquisition of 2-Methyl Serine Hydroxymethyl Transferase Gene Derived from *Silicibacter pomeroyi* DSM15171

Using genomic DNA of *Silicibacter pomeroyi* DSM15171 as a template, the amplified fragment of 1.3 kb including SEQ ID NO: 29 was obtained by PCR with primers Silici ATG EcoRI (SEQ ID NO: 27) and Silici_ter_Pst (SEQ ID NO: 28). The resulting fragment was treated with EcoRI/PstI, and inserted into pUC18 EcoRI/PstI site, which was designated pUCSHMT. Using this plasmid, *Escherichia coli* JM109 was transformed. The transformant was designated JM109/pUC-SHMT.

JM109/pUCSHMT was pre-cultured in LB medium containing 100 mg/l ampicillin and 0.1 mM IPTG at 37° C. for 16 hours. The resulting cells were collected by centrifugation and washed with 50 mM phosphoric acid buffer (pH7.4) containing 0.1 mM pyridoxal phosphate, and then a cell suspension was prepared with the same buffer. The cells were ultrasonically disrupted and centrifuged (18,000 g, 10 min., 4° C.) to obtain a supernatant as a cell-free extracted solution.

2-methyl serine hydroxymethyl transferase activity was measured in the supernatant. Separated formaldehyde was determined after reaction in the reaction mixture containing 50 mM Tris-HCl buffer (pH 7.4), 10 mM α-methyl-L-serine, and 0.1 mM pyridoxal phosphate at a reaction temperature 30° C. The measured value was 190 mU/mg.

Subsequently, using genomic DNA of *Silicibacter pomeroyi* DSM15171 as a template, the PCR product of approximately 1.3 kb length including SEQ ID NO: 29 was obtained by PCR with primers Silici ATG pQE30 BamHI (SEQ ID NO: 34) and Silici_ter_Pst (SEQ ID NO: 28). The resulting product was digested with BamHI-PstI to prepare DNA fragments, and the fragment was inserted into pQE30 BamHI-PstI site, thus obtaining a plasmid which was capable of forming 2-methyl serine hydroxymethyl transferase coupled with 6×His at the 5' terminal thereof. The plasmid was designated pQE30SHMT. Using this plasmid, *Escherichia coli* JM109 was transformed. The transformant was designated JM109/pQE30SHMT.

The obtained JM109/pQE30SHMT was cultured in the LB medium containing 100 mg/l ampicillin (LB+amp) at 30° C. for 14 hours, and further cultured for three hours after adding 1 mM IPTG. The resulting cells were collected by centrifugation and washed with 50 mM phosphoric acid buffer (pH 7.4) containing 0.1 mM pyridoxal phosphate, and then a cell suspension was prepared with the same buffer. The cells were ultrasonically disrupted and centrifuged (18,000 g, 10 min., 4° C.) to obtain a supernatant using QIAexprssionist (QIAGEN) in accordance with the attached protocol thereof. The obtained protein was designated His fused SHMT.

Using the obtained His fused SHMT, a reaction was performed in a 100 μL solution containing 10 mM formaldehyde, 100 mM L-alanine, 0.1 mM pyridoxal phosphate, 100 mM phosphoric acid buffer (pH 7.4) at 30° C. for 10 min. As formaldehyde, the highest quality of formaldehyde liquid product [code No.: 16223-55] from Nakarai Tesk was used. After the reaction, 200 μl of 1 mM aqueous copper sulfate was added into 100 μl of the reaction mixture, and HPLC analysis was performed using Sumichiral OA-6100 (Sumitomo Kagaku Analysis Center) (mobile phase: 0.5 mM aqueous copper sulfate, column temperature: 30° C., flow rate: 1 ml/min., detection: UV215 nm). The result showed that 0.367 mM α-methyl-L-serine was produced but no peak attributable to α-methyl-D-serine was detected.

Example 12

Production of α-Methyl-L-Serine with *Escherichia coli* Expressing 2-Methyl Serine Hydroxymethyl Transferase Gene Derived from *Variovorax paradoxus* Strain JM109/pTVVHMT01, JM109/pTVVHMT02, and JM109/pTVVHMT03 prepared in line with the aforementioned example were respectively pre-cultured in LB medium containing 100 mg/l ampicillin and 0.1 mM IPTG at 37° C. for 16 hours. The resulting cells were collected from 100 ml medium by centrifugation and washed with 100 mM phosphoric acid buffer (pH7.4) containing 0.1 mM pyridoxal phosphate.

The resulting cells were respectively suspended in 100 ml of a reaction mixture (150 mM L-alanine, 0.1 mM pyridoxal phosphate, 100 mM phosphoric acid buffer (pH7.4)). 50.5 ml of 300 mM aqueous formaldehyde was added to the reaction mixture at 30° C. over 24 hours while stirring. As formaldehyde, the highest quality of formaldehyde liquid product [code No.: 16223-55] from Nakarai Tesk was used. After the adding process, 50 μl of 1 mM aqueous copper sulfate and 100 μl of water were added to 50 μl of the reaction mixture, and HPLC analysis was performed using Sumichiral OA-6100 (Sumitomo Kagaku Analysis Center) (mobile phase: 0.5 mM aqueous copper sulfate, column temperature: 30° C., flow rate: 1 ml/min., detection: UV215 nm). The results are shown in Tabbe 5. It was confirmed that α-methyl-L-serine was produced but no peak attributable to α-methyl-D-serine was detected.

TABLE 5

| Strain | Yield of α-methyl-L-serine (mmol) |
|---|---|
| JM109/pTVVHMT01 | 1.2 |
| JM109/pTVVHMT02 | 5.3 |
| JM109/pTVVHMT03 | 13.7 |

Example 13

Preparation of a Strain Expressing 2-Methyl Serine Hydroxymethyl Transferase Derived from *Bosea* Sp. B2-R1 (AJ110407)

Fragments of 0.3 kb containing a promoter region of the trp operon on the chromosomal DNAs of *Eshcherichia coli* W3110 were amplified with oligonucleotide primers of SEQ ID NO: 31 and NO: 32, and then the resulting DNA fragments were ligated into pGEM-Teasy vector (Promega). In the ligation solution, *E. coli* JM109 was transformed, and a strain which contained the objective plasmid, in which the trp promoter had been inserted in the opposite direction of the lac promoter, was selected from the ampicillin-resistant strains. Subsequently, this plasmid was ligated with a DNA fragment containing trp promoter treated by EcoO109I/EcoRI and a product obtained by treating pUC19 (Takara) with EcoO109I/EcoRI. In the ligation solution, *E. coli* JM109 was transformed, and a strain containing the objective plasmid was selected from the ampicillin-resistant strains. This plasmid was treated with HindIII/PvuII and the resulting DNA fragment was ligated with DNA fragment of O.7 kb prepared by treating pKK223-3 (Amersham Pharmacia) with HindIII/HincI and containing the TrrnB terminator. Using this ligation solution, *Eshcherichia coli* JM109 was transformed, and a strain containing the objective plasmid was selected from the ampicillin-resistant strains. The plasmid was designated ptrp2. Using this ptrp2 as a template, 0.3 kb fragments containing the trp promoter were amplified with primers (SEQ ID NO: 31 and 33). In order to replace the promoter region of the ptrp2 with the resulting PCR product, a fragment prepared by digesting the resulting PCR product with EcoO109I/NdeI was ligated with a product prepared by treating ptrp2 with EcoO109I/NdeI. Using the resulting products, *Eshcherichia coli* JM109 was transformed, and a strain containing the objective plasmid was selected from the ampicillin-resistant strains. This plasmid was designated ptrp4. Subsequently, pTWV228 (TaKaRa) was treated with NdeI, and then the terminal thereof was blunt-ended. The resulting product was treated with AatII, obtaining a fragment of 1.9 kb. The resulting fragment was ligated with a 0.4 kb fragment prepared by treating ptrp4 AatII/HindIII and a 0.7 kb fragment prepared by treating pKK223-3 with PvuII/HindIII. Using the resulting ligation solution, *Escherichia coli* JM109 was transformed, and a strain containing the objective plasmid was selected from the ampicillin-resistant strains. This plasmid was designated ptrp13.

Using genomic DNA of *Bosea* sp. B2-R1 as a template, PCR was performed with primers B2-R1_Psh (SEQ ID NO: 24) and B2-R1_ter_Pst (SEQ ID NO: 25). The amplified fragment of 1.2 kb was obtained by PCR. The resulting fragment was treated with PshBI/PstI, and inserted into the ptrp13 NdeI/PstI site, which was designated ptrp13BHMT. Using this plasmid, *Escherichia coli* JM109 was transformed. The transformant was designated JM109/ptrp13BHMT.

JM109/ptrp13BMT, mentioned above, was cultured on LB agar medium (10 g/l peptone, 5 μl yeast extract, 10 μl NaCl) containing 100 μg/ml ampicillin at 30° C. for 24 hours. Subsequently, cells which were on one eighth of a plate were transferred to 50 mL LB medium (10 μl peptone, 5 μl yeast extract, 10 μl NaCl), and cultured at 30° C. for 16 hours on a shaker (120 rpm). Subsequently, 1 ml of the resulting culture was inoculated into a 300 ml medium containing the following composition, and then a batch culture was performed in a 1.0-liter volume fermentor while stirring at a revolution speed 700 rpm, and aeration (1/1 vvm). After the sugar was consumed, a 15 ml aliquot of the culture was inoculated into a 300 ml medium composed of the same composition, and then a culture was performed in the same type of fermentor under the conditions of stirring, aeration (1/1 vvm), sugar feeding and at 35° C. pH thereof was automatically adjusted to 7.0 by ammonium gas.

Composition of the Medium (g/l)
Glucose 25.0
$MgSO_4 \cdot 7H_2O$ 1.0
$(NH_4)_2SO_4$ 5.0
$H_3PO_4$ 3.5
$FeSO_4$ 7aq 0.05
$MnSO_4$ 7aq 0.05 Thiamine HCl 0.001
Pyridoxyne HCl 0.01
GD113 0.1
Ampicillin 0.1

Glucose and magnesium sulfate were individually sterilized. The pH of other elements was adjusted at 5.0 with KOH.

Composition of Feeding Sugar Solution (g/l)
Glucose 500.0
pH Not adjusted

Example 14

Production of α-Methyl-L-Serine with 2-Methyl Serine Hydroxymethyl Transferase Derived from *Bosea* Sp. B2-R1 (AJ110407)

Using the 30 ml of the resulting culture of JM109/ptrp13BHMT prepared in accordance with the aforementioned Example 13, the reaction to produce α-methyl-L-serine with 2-methyl serine hydroxymethyl transferase was conducted. 150 ml of 2400 mM formaldehyde aqueous solution was added to the 300 ml culture (1200 mM L-alanine, 0.1 mM pyridoxal phosphate, and 100 mM phosphoric acid buffer (pH 7.4), 10% of the cultured mixture of JM109/ptrp13BHMT) at 30° C. over 48 hours while stirring. As formaldehyde, the highest quality of formaldehyde liquid product [code No.: 16223-55] from Nakarai Tesk was used. After the adding process, 950 μl of 1 mM aqueous copper sulfate was added to 50 ml of the resulting solution. After 5-fold dilution with water, HPLC analysis was performed using Sumichiral OA-6100 (Sumitomo Kagaku Analysis Center) (mobile phase: 0.5 mM aqueous copper sulfate, column temperature: 30° C., flow rate: 1 ml/min., detection: UV215 nm). The result showed that 327.3 mmol α-methyl-L-serine was produced but no peak attributable to α-methyl-D-serine was detected.

Example 15

Purification of α-Methyl-L-Serine

The cells are roughly removed from the resulting reaction mixture prepared in accordance with Example 14. 3.3 g sulfuric acid was added to the 451 g resulting reaction mixture (α-methyl-L-serine: 9.08%) to adjust to pH 3, and then dissolved proteins were flocculated by heating at 50° C. for 1 hour. The resulting product was filtered with 0.2 μm MF, obtaining a 482 g solution α-methyl-L-serine: 8.45%, D-alanine: 0.13%, L-alanine: 0.08%) including residual washing water. 165 g of this solution was diluted with water to 5% α-methyl-L-serine. After the dilution, the solution was fed into a resin column filled with 120 ml H-type strong-acid cation exchange resin (Bayel, Lewatit S-1468), thus adsorbing α-methyl-L-serine. After washing with twofold volume of water of the resin, 352 g of aqueous solution (Content of α-methyl serine: approximately 3.8%) was obtained by elution using 1 M ammonia water.

The resulting solution was evaporated under reduced pressure to roughly remove ammonia. The pH of the solution at this stage was approximately 8.2. To remove any remaining cations, the solution was passed through a column filled with 20 ml H-type weak-acid cation exchange resin (IONAC, A-365), thus obtaining 204 g flow-through solution including the washing solution, with a pH was 5.2. Subsequently, the flow-through solution was condensed. The condensing process was stopped when crystals began to precipitate out. At this moment, the volume weight of the solution was 35.55 g α-methyl-L-serine: 37.2%). Then, crystallization by adding poor solvent was performed by adding 67 g methanol at room temperature. Then, after maturing at 10° C. for 1 hour while stirring, crystals were separated and washed with 12 g of 75% methanol aqueous solution. The obtained wet crystal was dried under reduced pressure at 40° C., resulting in 12.13 g of dried crystal. The content of α-methyl-L-serine was 100.7% compared to a commercially available standard. The resulting crystal contained 0.06% D-alanine and 0.05% L-alanine as impurities.

Example 16

Production of α-Ethyl-L-Serine with *Esherichia coli* Expressing 2-Methyl Serine Hydroxymethyl Transferase Gene Derived from *Bosea* Sp JM109/pUCBHMT as cell-enzyme was suspended in 100 ml solution mixture (150 mM L-2-amino-n-butyric acid, 0.1 mM pyridoxal phosphate, 100 mM phosphoric acid buffer (pH 7.4)). 50.5 ml of 300 mM aqueous formaldehyde was added to the reaction mixture at 30° C. over 24 hours while stirring. As formaldehyde, the highest quality of formaldehyde liquid product [code No.: 16223-55] from Nakarai Tesk was used. After the cell separation (8000 g, 10 min), the resulting mixture (50 ml containing 632 mg of 4.75 mmol α-ethyl-serine) was applied to Mega Bond Elut SCX (10G) (Varian, Inc) which had been previously activated with 50 ml methanol and equilibrated with 100 ml $H_2O$. Then, after washing with 100 ml water, fractions of 2.5 ml were each eluted with 0.5 N—HCl. HPLC analysis was performed for each fraction to confirm the amount of α-ethyl-serine/(α-ethyl serine+L-2-amino-n-butyric acid), thus obtaining the separated fraction with more than 99%. Non-separated fractions were evaporated to dryness, and then dissolved into approximately 10 ml water. The pH of the resulting solution was adjusted to around pH 7.0 by NaOH, and again the separation process was performed in accordance with the same manner mentioned above. This operation was repeated twice to collect the separated fractions, and these separated fractions were evaporated to dryness. The resulting product was dissolved into approximately 100 ml water and anion exchange resin (DEAE-cellulose, whatman) was added therein, and its pH was adjusted to around 6.0. After that, the resin was removed by filtration. Acetone was dropped into the resulting filtrate to precipitate crystals. The precipitated crystals were dried, obtaining white crystals (348 mg, 2.6 mmol). The structure of the obtained crystals was determined by NMR spectral and ESI-MS analysis, and then the optical rotation thereof was measured by a optical rotation measuring device (DIP-370) manufactured by Nippon Bunko ($[a]_D^{20}$=-3.4±0.4 (c=1, 5N—HCl), $[a]_D^{20}$=-4.5±0.04 (C=10, 5N—HCl)). It was confirmed that the major product of the enzymatic reaction had a (−)-form, i.e., (s)-form in reference to values described in the literature (Journal of Peptide Science, 2001, 7, 619-625; Tetrahedron Letters, 1988, 29, 235-238).

After the cell separation (8000 g, 10 min), 5 mmol $NaHCO_3$ was added to the resulting mixture (25 ml containing 316 mg of 2.38 mmol α-ethyl-serine), and the pH was adjusted to 9.5 under ice cooling. 2.38 mmol Benzoyl chloride dissolved in 10 ml acetone was dropped therein over 1 hour while maintaining the pH at 9-10. After that, the reaction was performed for 3 hours at room temperature, and then HCl was added therein to adjust to pH 2.0. After EtOAc (10 ml×3) extraction and dehydration with $MgSO_4$, the reaction product was evaporated to dryness. According to HPLC analysis, it was confirmed that the residue included a large amount of benzoic acid. For that reason, the product was dissolved in methanol and separation was performed by TLC (PLC plate 20×20 cm, Silica gel $60F_{254}$ 2 mm (Merck), developing solvent: EtOAc/AcOH=20/1). After the detection step by UV irradiation, silica gel was collected by scraping, and subjected to extraction with methanol (100 ml). The resulting product was evaporated to dryness, thus obtaining white crystals. The white crystals were crystallized again by the following steps: adding a small amount of water thereto and adjusting the pH to around 8.0 with NaOH to dissolve them; and dropping HCl and adjusting the pH to around 2.0, to obtain the crystals again. The resulting crystals were separated by filtration. After the filtered crystals were dried, they were dissolved in a small amount of 2-propanol, and then hexane was dropped therein to crystallize again, thus obtaining 110 mg standard product (0.46 mmol). The result of the HPLC analysis indicated 99% area. The structure was determined by NMR spectral and ESI-MS analysis, and then the optical rotation was measured ($[α]_D^{20}$=-11.4±0.2 (C=1, methanol)). It was confirmed that the major product of the enzymatic reaction had (−)-form, i.e., (s)-form in reference to values described in the literature (Journal of Peptide Science, 2001, 7, 619-625).

Example 17

Production of α-Methyl Threonine with 2-Methyl Serine Hydroxymethyl Transferase Derived from *Ralstonia* sp. A11 (AJ110405)

50 μl of purified enzyme solution prepared in accordance with Example 2 was added to a solution composed of 51 mM acetaldehyde, 50 mM L-alanine, 0.1 mM pyridoxal phosphate, and 100 mM phosphoric acid buffer (pH 7.4). The reaction was performed at 30° C. for 17.5 hours. After the reaction, a supernatant was prepared by centrifugation (18,000 g, 10 min, 4° C.). The peak attributed to the molecular ion of α-methyl threonine was detected by ESI-MS analysis in the obtained supernatant.

INDUSTRIAL APPLICABILITY

The method of the present invention is useful in industries involving in amino acid production. It is expected that the present invention would contribute to the production of various types of serine derivatives and optically active amino acids, and specifically, the method may be used in producing, for example, intermediates for drugs and medicals.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

Free Text of Sequence Listing
SEQ ID NO: 1: primer
SEQ ID NO: 2: primer
SEQ ID NO: 3: primer
SEQ ID NO: 6: primer
SEQ ID NO: 7: primer
SEQ ID NO: 10: primer
SEQ ID NO: 11: primer
SEQ ID NO: 12: primer
SEQ ID NO: 13: primer
SEQ ID NO: 16: primer
SEQ ID NO: 17: primer
SEQ ID NO: 20: primer
SEQ ID NO: 21: primer
SEQ ID NO: 24: primer
SEQ ID NO: 25: primer
SEQ ID NO: 26: primer
SEQ ID NO: 27: primer
SEQ ID NO: 28: primer
SEQ ID NO: 31: primer
SEQ ID NO: 32: primer
SEQ ID NO: 33: primer
SEQ ID NO: 34: primer

The invention claimed is:

1. A method for producing an L-serine derivative of formula (III):

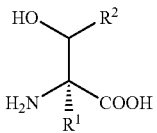

comprising reacting an L-α-amino acid of formula (I):

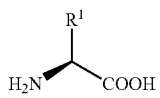

with an aldehyde of formula (II):

in the presence of an enzyme,
wherein R¹ is selected from the group consisting of an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, wherein these groups may be either linear or branched and may have a substituent, and
wherein R² is selected from the group consisting of a hydrogen, an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, wherein these groups may be either linear or branched and may have a substituent;
wherein said enzyme is a protein selected from the group consisting of:
(A) a protein comprising the amino acid sequence of SEQ ID NO: 23; and
(B) a protein comprising an amino acid sequence which has variation in the amino acid sequence of SEQ ID NO: 23, wherein said variation is selected from the group consisting of substitution, deletion, insertion, addition, inversion, and combinations thereof, of amino acids in said sequence, and wherein said protein is at least 90% homologous with the sequence of SEQ ID NO. 23 and is able to catalyze the reaction to form said L-serine derivative of formula (III).

2. The method for producing the L-serine derivative according to claim 1, wherein said enzyme is derived from and native to the microorganism *Bosea*.

3. The method for producing the L-serine derivative according to claim 1, wherein said L-α-amino acid is L-α-alanine, and said L-serine derivative is α-methyl-L-serine.

4. The method for producing the L-serine derivative according to claim 1, wherein said L-α-amino acid is L-2-amino-n-butyric acid, and said L-serine derivative is α-ethyl-L-serine.

5. The method for producing the L-serine derivative according to claim 1, wherein said L-α-amino acid is L-α-alanine, and said L-serine derivative is α-methyl-L-threonine.

6. The method of claim 1, wherein said protein is at least 95% homologous with the sequence of SEQ ID NO. 23 and is able to catalyze the reaction to form said L-serine derivative of formula (III).

7. A method for producing an L-serine derivative of formula (III):

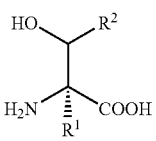

comprising reacting an L-α-amino acid of formula (I):

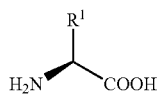

with an aldehyde of formula (II):

in the presence of an enzyme,
wherein R¹ is selected from the group consisting of an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, wherein these groups may be either linear or branched and may have a substituent, and
wherein R² is selected from the group consisting of a hydrogen, an alkyl group with 1 to 6 carbons, an aryl group with 6 to 14 carbons, a cycloalkyl group with 3 to 10 carbons, an aralkyl group with 7 to 19 carbons, an alkoxyalkyl group with 2 to 11 carbons, a group containing a hetero atom in the carbon skeleton thereof, and a group containing a carbon-carbon unsaturated bond in the carbon skeleton thereof, wherein these groups may be either linear or branched and may have a substituent;

wherein said enzyme is a protein selected from the group consisting of:
(A) a protein comprising the amino acid sequence encoded by the nucleotide sequence of SEQ ID NO: 22; and
(B) a protein comprising an amino acid sequence encoded by a nucleotide sequence that is at least 95% or more homologous with the sequence of SEQ ID NO: 22, and said protein is able to catalyze the reaction to form said L-serine derivative of formula (III).

8. The method for producing the L-serine derivative according to claim 6, wherein said enzyme is derived from and native to the microorganism *Bosea*.

9. The method for producing the L-serine derivative according to claim 6, wherein said L-α-amino acid is L-α-alanine, and said L-serine derivative is α-methyl-L-serine.

10. The method for producing the L-serine derivative according to claim 6, wherein said L-α-amino acid is L-2-amino-n-butyric acid, and said L-serine derivative is α-ethyl-L-serine.

11. The method for producing the L-serine derivative according to claim 6, wherein said L-α-amino acid is L-2-amino-n-butyric acid, and said L-serine derivative is α-ethyl-L-serine.

* * * * *

SEQUENCE LISTING

```
<160> NUMBER OF SEQ ID NOS: 34

<210> SEQ ID NO 1
<211> LENGTH: 30
<212> TYPE: PRT
<213> ORGANISM: Ralstonia sp.
```

<400> SEQUENCE: 1

Met Leu Asn Ala Arg Pro Trp Val Pro Glu Gly Pro Glu Glu Tyr Met
1               5                   10                  15

Gln Ala Leu Ala Lys Arg Phe Ala Gly Gln Thr Pro Asp Gln
            20                  25                  30

<210> SEQ ID NO 2
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (18)..(18)
<223> OTHER INFORMATION: a, c, g or t
<220> FEATURE:
<221> NAME/KEY: misc_feature
<222> LOCATION: (21)..(21)
<223> OTHER INFORMATION: a, c, g or t

<400> SEQUENCE: 2
gcytgcatrt aytcytcngg ncc                                         23

<210> SEQ ID NO 3
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: a, c, g or t
<220> FEATURE:
<221> NAME/KEY: misc_feature
<222> LOCATION: (6)..(6)
<223> OTHER INFORMATION: a, c, g or t
<220> FEATURE:
<221> NAME/KEY: misc_feature
<222> LOCATION: (12)..(12)
<223> OTHER INFORMATION: a, c, g or t
<220> FEATURE:
<221> NAME/KEY: misc_feature
<222> LOCATION: (18)..(18)
<223> OTHER INFORMATION: a, c, g or t

<400> SEQUENCE: 3
tcnggnaccc anggscgngc rtt                                         23

<210> SEQ ID NO 4
<211> LENGTH: 1317
<212> TYPE: DNA
<213> ORGANISM: Ralstonia sp.
<220> FEATURE:
<221> NAME/KEY: CDS
<222> LOCATION: (1)..(1317)

<400> SEQUENCE: 4 atg ttg aac gca cgc ccc tgg gtg ccg gaa ggt ccc gaa gaa tat atg      48
Met Leu Asn Ala Arg Pro Trp Val Pro Glu Gly Pro Glu Glu Tyr Met
1               5                   10                  15 caa gct ctg gcc aag cgt ttt gct ggc cag acc cct gac cag aac gaa      96
Gln Ala Leu Ala Lys Arg Phe Ala Gly Gln Thr Pro Asp Gln Asn Glu
            20                  25                  30 cgc gac ctg ctc gcc ttc gtt gaa gag aat cgc gtc att cac gaa cgt     144
Arg Asp Leu Leu Ala Phe Val Glu Glu Asn Arg Val Ile His Glu Arg
        35                  40                  45

```
gat tgc ttc aat ctg aac ccg gcc acc aat gcc atc aat ccg aag gcc      192
Asp Cys Phe Asn Leu Asn Pro Ala Thr Asn Ala Ile Asn Pro Lys Ala
 50                  55                  60 gag gcg atg ctg gcc tcc ggt gtc ggt tcg cgg cca tcg ctc ggc tac      240
Glu Ala Met Leu Ala Ser Gly Val Gly Ser Arg Pro Ser Leu Gly Tyr
 65                  70                  75                  80 ccg ggc gac aag tac gag atg ggc ctg gag ggc gtg gag aag att gag      288
Pro Gly Asp Lys Tyr Glu Met Gly Leu Glu Gly Val Glu Lys Ile Glu
                 85                  90                  95 gtg ttg gcg gcg gaa ctc gta gcc gag gtg ttc ggt gcc aag tac gcc      336
Val Leu Ala Ala Glu Leu Val Ala Glu Val Phe Gly Ala Lys Tyr Ala
            100                 105                 110 gag ttg cgt gtt gcc tcg ggc gcc ctc gcc aat ctc tac gcc tac atg      384
Glu Leu Arg Val Ala Ser Gly Ala Leu Ala Asn Leu Tyr Ala Tyr Met
        115                 120                 125 att gcc gcc aag ccg ggc gat acg gtg ttc gtc ccc agc gct acc atc      432
Ile Ala Ala Lys Pro Gly Asp Thr Val Phe Val Pro Ser Ala Thr Ile
    130                 135                 140 ggc ggc cac ttc agc cac cat gcg aat ggg gcg gcc ggc atg tac gga      480
Gly Gly His Phe Ser His His Ala Asn Gly Ala Ala Gly Met Tyr Gly
145                 150                 155                 160 gtc aat tcg tac ctg atg ccg ttc gat gcc gac aag tac acc gtc gac      528
Val Asn Ser Tyr Leu Met Pro Phe Asp Ala Asp Lys Tyr Thr Val Asp
                165                 170                 175 gtc gac cgt ctg cgc gag gat gca cgc agg ctc aag ccc aag atg att      576
Val Asp Arg Leu Arg Glu Asp Ala Arg Arg Leu Lys Pro Lys Met Ile
            180                 185                 190 acc ctg ggc aac agc ctc aac ctc ttt ccc cat ccc atc aag gag gtg      624
Thr Leu Gly Asn Ser Leu Asn Leu Phe Pro His Pro Ile Lys Glu Val
        195                 200                 205 agg gag att gcc gac gaa atc ggc gcg ctg gtc ctc ttt gac gcg gcg      672
Arg Glu Ile Ala Asp Glu Ile Gly Ala Leu Val Leu Phe Asp Ala Ala
    210                 215                 220 cat ctt tgc gga ctg att gcc ggc cac tcc tgg cag cag ccg ctg gaa      720
His Leu Cys Gly Leu Ile Ala Gly His Ser Trp Gln Gln Pro Leu Glu
225                 230                 235                 240 gaa ggt gct cat ctc atg acc ttg agc acg tat aaa agc ctt gcc ggc      768
Glu Gly Ala His Leu Met Thr Leu Ser Thr Tyr Lys Ser Leu Ala Gly
                245                 250                 255 ccc gcc ggc ggc ctt atc gtg acc aac gac gct gag gtt gcc aag cgc      816
Pro Ala Gly Gly Leu Ile Val Thr Asn Asp Ala Glu Val Ala Lys Arg
            260                 265                 270 ctg gac aca gtt gcc tat ccg ggc atg acc gcg aac ttc gat tcg gcc      864
Leu Asp Thr Val Ala Tyr Pro Gly Met Thr Ala Asn Phe Asp Ser Ala
        275                 280                 285 cgc tcg gca tcc att gcg atg acg atg ctg gac tgg caa gtc tat ggc      912
Arg Ser Ala Ser Ile Ala Met Thr Met Leu Asp Trp Gln Val Tyr Gly
    290                 295                 300 cgt gag tac gct gcc gag atg gtg cgt acc agc aag gcc ttc gcc gaa      960
Arg Glu Tyr Ala Ala Glu Met Val Arg Thr Ser Lys Ala Phe Ala Glu
305                 310                 315                 320 gcg ctg gtc aag gag ggg ctc ccg gtg ttt gcg cgc gac cgc ggt atc     1008
Ala Leu Val Lys Glu Gly Leu Pro Val Phe Ala Arg Asp Arg Gly Ile
                325                 330                 335 acg aca tct cat cag ttc gcg att gaa gcg cat gac ttc ggg ggg ggg     1056
Thr Thr Ser His Gln Phe Ala Ile Glu Ala His Asp Phe Gly Gly Gly
            340                 345                 350 cag gcg atg gca aag ctt ctg cgc cgc gcg aac att ctc gcg tgc gga     1104
Gln Ala Met Ala Lys Leu Leu Arg Arg Ala Asn Ile Leu Ala Cys Gly
```

-continued

```
              355                 360                 365
atc ggc tta cca ctt ccg gaa atc gcg ggg gac gtg aac ggt ctg cgt    1152
Ile Gly Leu Pro Leu Pro Glu Ile Ala Gly Asp Val Asn Gly Leu Arg
        370                 375                 380 atg gga acg ccc gag ctc gta cgt tgg gga atg cgt agc gag cac atg    1200
Met Gly Thr Pro Glu Leu Val Arg Trp Gly Met Arg Ser Glu His Met
385                 390                 395                 400 cca caa ctc gct aag ttc atc gca gac gtg ctg ctg ggt cgc cag gtg    1248
Pro Gln Leu Ala Lys Phe Ile Ala Asp Val Leu Leu Gly Arg Gln Val
                405                 410                 415 cca gaa gaa gtc gcg cca gcc gtc acc gac tac cgt cga cag ttc aac    1296
Pro Glu Glu Val Ala Pro Ala Val Thr Asp Tyr Arg Arg Gln Phe Asn
            420                 425                 430 aag ctg cat ttc ctg cgc taa                                        1317
Lys Leu His Phe Leu Arg
        435

<210> SEQ ID NO 5
<211> LENGTH: 438
<212> TYPE: PRT
<213> ORGANISM: Ralstonia sp.

<400> SEQUENCE: 5

Met Leu Asn Ala Arg Pro Trp Val Pro Glu Gly Pro Glu Glu Tyr Met
1               5                   10                  15

Gln Ala Leu Ala Lys Arg Phe Ala Gly Gln Thr Pro Asp Gln Asn Glu
            20                  25                  30

Arg Asp Leu Leu Ala Phe Val Glu Glu Asn Arg Val Ile His Glu Arg
        35                  40                  45

Asp Cys Phe Asn Leu Asn Pro Ala Thr Asn Ala Ile Asn Pro Lys Ala
    50                  55                  60

Glu Ala Met Leu Ala Ser Gly Val Gly Ser Arg Pro Ser Leu Gly Tyr
65                  70                  75                  80

Pro Gly Asp Lys Tyr Glu Met Gly Leu Glu Gly Val Glu Lys Ile Glu
                85                  90                  95

Val Leu Ala Ala Glu Leu Val Ala Glu Val Phe Gly Ala Lys Tyr Ala
            100                 105                 110

Glu Leu Arg Val Ala Ser Gly Ala Leu Ala Asn Leu Tyr Ala Tyr Met
        115                 120                 125

Ile Ala Ala Lys Pro Gly Asp Thr Val Phe Val Pro Ser Ala Thr Ile
    130                 135                 140

Gly Gly His Phe Ser His His Ala Asn Gly Ala Ala Gly Met Tyr Gly
145                 150                 155                 160

Val Asn Ser Tyr Leu Met Pro Phe Asp Ala Asp Lys Tyr Thr Val Asp
                165                 170                 175

Val Asp Arg Leu Arg Glu Asp Ala Arg Arg Leu Lys Pro Lys Met Ile
            180                 185                 190

Thr Leu Gly Asn Ser Leu Asn Leu Phe Pro His Pro Ile Lys Glu Val
        195                 200                 205

Arg Glu Ile Ala Asp Glu Ile Gly Ala Leu Val Leu Phe Asp Ala Ala
    210                 215                 220

His Leu Cys Gly Leu Ile Ala Gly His Ser Trp Gln Gln Pro Leu Glu
225                 230                 235                 240

Glu Gly Ala His Leu Met Thr Leu Ser Thr Tyr Lys Ser Leu Ala Gly
                245                 250                 255

Pro Ala Gly Gly Leu Ile Val Thr Asn Asp Ala Glu Val Ala Lys Arg
```

-continued

```
            260                 265                 270
Leu Asp Thr Val Ala Tyr Pro Gly Met Thr Ala Asn Phe Asp Ser Ala
        275                 280                 285

Arg Ser Ala Ser Ile Ala Met Thr Met Leu Asp Trp Gln Val Tyr Gly
        290                 295                 300

Arg Glu Tyr Ala Ala Glu Met Val Arg Thr Ser Lys Ala Phe Ala Glu
305                 310                 315                 320

Ala Leu Val Lys Glu Gly Leu Pro Val Phe Ala Arg Asp Arg Gly Ile
                325                 330                 335

Thr Thr Ser His Gln Phe Ala Ile Glu Ala His Asp Phe Gly Gly Gly
            340                 345                 350

Gln Ala Met Ala Lys Leu Leu Arg Arg Ala Asn Ile Leu Ala Cys Gly
        355                 360                 365

Ile Gly Leu Pro Leu Pro Glu Ile Ala Gly Asp Val Asn Gly Leu Arg
    370                 375                 380

Met Gly Thr Pro Glu Leu Val Arg Trp Gly Met Arg Ser Glu His Met
385                 390                 395                 400

Pro Gln Leu Ala Lys Phe Ile Ala Asp Val Leu Leu Gly Arg Gln Val
                405                 410                 415

Pro Glu Glu Val Ala Pro Ala Val Thr Asp Tyr Arg Arg Gln Phe Asn
            420                 425                 430

Lys Leu His Phe Leu Arg
        435

<210> SEQ ID NO 6
<211> LENGTH: 33
<212> TYPE: DNA
<213> ORGANISM: Artificial
<220> FEATURE:
<223> OTHER INFORMATION: primer

<400> SEQUENCE: 6
cggaattcga gaggaactga gcatgttgaa cgc                                33

<210> SEQ ID NO 7
<211> LENGTH: 33
<212> TYPE: DNA
<213> ORGANISM: Artificial
<220> FEATURE:
<223> OTHER INFORMATION: primer

<400> SEQUENCE: 7
aactgcagtt agcgcaggaa atgcagcttg ttg                                33

<210> SEQ ID NO 8
<211> LENGTH: 1326
<212> TYPE: DNA
<213> ORGANISM: Variovorax Paradoxus
<220> FEATURE:
<221> NAME/KEY: CDS
<222> LOCATION: (1)..(1326)

<400> SEQUENCE: 8 atg cct gcc gcc gcc ctg caa cgc cgc ccc tgg gtt ccc gcc gcc agc      48
Met Pro Ala Ala Ala Leu Gln Arg Arg Pro Trp Val Pro Ala Ala Ser
1               5                   10                  15 gaa gac cat gtg ctt tcc atc gcc gcc gat gcc gct gcg cgc gat gcg      96
Glu Asp His Val Leu Ser Ile Ala Ala Asp Ala Ala Ala Arg Asp Ala
            20                  25                  30 gcg agc gtc gcc gtc gag atc gaa cgg ctg gtg gcc gag aac cac cgc     144
```

-continued

| | | |
|---|---|---|
| Ala Ser Val Ala Val Glu Ile Glu Arg Leu Val Ala Glu Asn His Arg<br>35 40 45 | | |
| atc cac gac gtc gac ggc ctg aac ctc aac ccc gcc acc aac gtg atg<br>Ile His Asp Val Asp Gly Leu Asn Leu Asn Pro Ala Thr Asn Val Met<br>50 55 60 | 192 | |
| aac ccg gcc gcc gaa gct ttg ctg tcg cgc ggg ctc ggc tcg cgc ccg<br>Asn Pro Ala Ala Glu Ala Leu Leu Ser Arg Gly Leu Gly Ser Arg Pro<br>65 70 75 80 | 240 | |
| tcg ctg ggc tac ccg ggc gac aag tac gag atg ggg ctc gag gcc atc<br>Ser Leu Gly Tyr Pro Gly Asp Lys Tyr Glu Met Gly Leu Glu Ala Ile<br>85 90 95 | 288 | |
| gag cgc atc gag gtc gtc gcg gcc gaa ctc gca gcc gaa gtg ttc ggc<br>Glu Arg Ile Glu Val Val Ala Ala Glu Leu Ala Ala Glu Val Phe Gly<br>100 105 110 | 336 | |
| gcg aag ttc gcc gag gtg cgc gtg agc tcc ggc gcg ctg tcg aat ctc<br>Ala Lys Phe Ala Glu Val Arg Val Ser Ser Gly Ala Leu Ser Asn Leu<br>115 120 125 | 384 | |
| tac gtg ttc atg gcg acc tgc cgg ccc ggc gac acg atc atc gtg ccg<br>Tyr Val Phe Met Ala Thr Cys Arg Pro Gly Asp Thr Ile Ile Val Pro<br>130 135 140 | 432 | |
| ccg ccc agc atc ggt ggc cat gtc acg cac cat gcg gcg ggc gcg gcg<br>Pro Pro Ser Ile Gly Gly His Val Thr His His Ala Ala Gly Ala Ala<br>145 150 155 160 | 480 | |
| ggg ctc tat ggc ctg aag ccg gtt tcc gcg ccg gtc gat gcc gac ggc<br>Gly Leu Tyr Gly Leu Lys Pro Val Ser Ala Pro Val Asp Ala Asp Gly<br>165 170 175 | 528 | |
| tac acg gtc gac gtg gct gcg ctg gcg aag ttg gcg ggc gaa gtg aag<br>Tyr Thr Val Asp Val Ala Ala Leu Ala Lys Leu Ala Gly Glu Val Lys<br>180 185 190 | 576 | |
| ccg aag ctc atc acc atc ggc ggc agc ctg aac ctg ttc ccg cat ccg<br>Pro Lys Leu Ile Thr Ile Gly Gly Ser Leu Asn Leu Phe Pro His Pro<br>195 200 205 | 624 | |
| gtg ccc gcg atc cgc gag atc gcc gac ggc gtg ggc gcg aag ctg ctg<br>Val Pro Ala Ile Arg Glu Ile Ala Asp Gly Val Gly Ala Lys Leu Leu<br>210 215 220 | 672 | |
| ttc gac gcc gcg cac ctc tcg ggc atg gtg gcc ggc aag gcg tgg ccg<br>Phe Asp Ala Ala His Leu Ser Gly Met Val Ala Gly Lys Ala Trp Pro<br>225 230 235 240 | 720 | |
| cag ccg ctg gag cag ggc gcg cat gcg atc acc atg agc acc tac aag<br>Gln Pro Leu Glu Gln Gly Ala His Ala Ile Thr Met Ser Thr Tyr Lys<br>245 250 255 | 768 | |
| agc ctg ggc ggc ccg gcg ggc ggg ctg atc gtg tcg aac gac gcg gcg<br>Ser Leu Gly Gly Pro Ala Gly Gly Leu Ile Val Ser Asn Asp Ala Ala<br>260 265 270 | 816 | |
| ctg atg gag cgc atc gac gcc atc gcg tat ccc ggc ctc acg gcc aat<br>Leu Met Glu Arg Ile Asp Ala Ile Ala Tyr Pro Gly Leu Thr Ala Asn<br>275 280 285 | 864 | |
| tcg gat gcg ggc cgc acg gcc gca ctg gcg cgt agc ctg ctc gac tgg<br>Ser Asp Ala Gly Arg Thr Ala Ala Leu Ala Arg Ser Leu Leu Asp Trp<br>290 295 300 | 912 | |
| aaa gtg cat ggc gtg gcc tat gca gcc gcg atg cgc gag acc gcg cag<br>Lys Val His Gly Val Ala Tyr Ala Ala Ala Met Arg Glu Thr Ala Gln<br>305 310 315 320 | 960 | |
| gcg ctg gcg cgc gca ctc gat gcg cgg ggc ctg ccc gtg ttt gtc aag<br>Ala Leu Ala Arg Ala Leu Asp Ala Arg Gly Leu Pro Val Phe Val Lys<br>325 330 335 | 1008 | |
| gcg cgc ggc ttc acg cag tcg cat cag ctc gcg gtc gaa gcg gcg cgc<br>Ala Arg Gly Phe Thr Gln Ser His Gln Leu Ala Val Glu Ala Ala Arg<br>340 345 350 | 1056 | |

```
tgg ggc ggt ggg cag cac gcg gcg aag aag atc gcg caa ggc ggc ctg    1104
Trp Gly Gly Gly Gln His Ala Ala Lys Lys Ile Ala Gln Gly Gly Leu
        355                 360                 365 ctg gcc tgc ggc atc ggc ctg ccg atc gcg ccc gtg gaa ggc gac atc    1152
Leu Ala Cys Gly Ile Gly Leu Pro Ile Ala Pro Val Glu Gly Asp Ile
    370                 375                 380 aac ggc ctg cgg ctc ggc gtg ccc gag atc gtg cgc ctg ggc ttc acg    1200
Asn Gly Leu Arg Leu Gly Val Pro Glu Ile Val Arg Leu Gly Phe Thr
385                 390                 395                 400 ccc gac gac atg ccg cag ctg gcc gac tgg atc gcg cga gcg ctc gaa    1248
Pro Asp Asp Met Pro Gln Leu Ala Asp Trp Ile Ala Arg Ala Leu Glu
                405                 410                 415 ggc gac gca gct tct gtg gcc gcc gaa gtg cga gag cgc cgc acg cac    1296
Gly Asp Ala Ala Ser Val Ala Ala Glu Val Arg Glu Arg Arg Thr His
            420                 425                 430 ctc ggc gaa ctg cgc tac atc gtg cgc tga                            1326
Leu Gly Glu Leu Arg Tyr Ile Val Arg
        435                 440

<210> SEQ ID NO 9
<211> LENGTH: 441
<212> TYPE: PRT
<213> ORGANISM: Variovorax Paradoxus

<400> SEQUENCE: 9

Met Pro Ala Ala Ala Leu Gln Arg Arg Pro Trp Val Pro Ala Ala Ser
1               5                   10                  15

Glu Asp His Val Leu Ser Ile Ala Ala Asp Ala Ala Arg Asp Ala
            20                  25                  30

Ala Ser Val Ala Val Glu Ile Glu Arg Leu Val Ala Glu Asn His Arg
        35                  40                  45

Ile His Asp Val Asp Gly Leu Asn Leu Asn Pro Ala Thr Asn Val Met
    50                  55                  60

Asn Pro Ala Ala Glu Ala Leu Leu Ser Arg Gly Leu Gly Ser Arg Pro
65                  70                  75                  80

Ser Leu Gly Tyr Pro Gly Asp Lys Tyr Glu Met Gly Leu Glu Ala Ile
                85                  90                  95

Glu Arg Ile Glu Val Val Ala Ala Glu Leu Ala Ala Glu Val Phe Gly
            100                 105                 110

Ala Lys Phe Ala Glu Val Arg Val Ser Ser Gly Ala Leu Ser Asn Leu
        115                 120                 125

Tyr Val Phe Met Ala Thr Cys Arg Pro Gly Asp Thr Ile Ile Val Pro
    130                 135                 140

Pro Pro Ser Ile Gly Gly His Val Thr His Ala Ala Gly Ala Ala
145                 150                 155                 160

Gly Leu Tyr Gly Leu Lys Pro Val Ser Ala Pro Val Asp Ala Asp Gly
                165                 170                 175

Tyr Thr Val Asp Val Ala Ala Leu Ala Lys Leu Ala Gly Glu Val Lys
            180                 185                 190

Pro Lys Leu Ile Thr Ile Gly Gly Ser Leu Asn Leu Phe Pro His Pro
        195                 200                 205

Val Pro Ala Ile Arg Glu Ile Ala Asp Gly Val Gly Ala Lys Leu Leu
    210                 215                 220

Phe Asp Ala Ala His Leu Ser Gly Met Val Ala Gly Lys Ala Trp Pro
225                 230                 235                 240

Gln Pro Leu Glu Gln Gly Ala His Ala Ile Thr Met Ser Thr Tyr Lys
                245                 250                 255
```

Ser Leu Gly Gly Pro Ala Gly Gly Leu Ile Val Ser Asn Asp Ala Ala
                260                 265                 270

Leu Met Glu Arg Ile Asp Ala Ile Ala Tyr Pro Gly Leu Thr Ala Asn
            275                 280                 285

Ser Asp Ala Gly Arg Thr Ala Ala Leu Ala Arg Ser Leu Leu Asp Trp
        290                 295                 300

Lys Val His Gly Val Ala Tyr Ala Ala Ala Met Arg Glu Thr Ala Gln
305                 310                 315                 320

Ala Leu Ala Arg Ala Leu Asp Ala Arg Gly Leu Pro Val Phe Val Lys
                325                 330                 335

Ala Arg Gly Phe Thr Gln Ser His Gln Leu Ala Val Glu Ala Ala Arg
            340                 345                 350

Trp Gly Gly Gly Gln His Ala Ala Lys Lys Ile Ala Gln Gly Gly Leu
        355                 360                 365

Leu Ala Cys Gly Ile Gly Leu Pro Ile Ala Pro Val Glu Gly Asp Ile
370                 375                 380

Asn Gly Leu Arg Leu Gly Val Pro Glu Ile Val Arg Leu Gly Phe Thr
                385                 390                 395                 400

Pro Asp Asp Met Pro Gln Leu Ala Asp Trp Ile Ala Arg Ala Leu Glu
            405                 410                 415

Gly Asp Ala Ala Ser Val Ala Ala Glu Val Arg Glu Arg Thr His
        420                 425                 430

Leu Gly Glu Leu Arg Tyr Ile Val Arg
            435                 440

<210> SEQ ID NO 10
<211> LENGTH: 32
<212> TYPE: DNA
<213> ORGANISM: Artificial
<220> FEATURE:
<223> OTHER INFORMATION: primer

<400> SEQUENCE: 10
cacacaggaa acagcatatg gccatgatta cg                                   32

<210> SEQ ID NO 11
<211> LENGTH: 32
<212> TYPE: DNA
<213> ORGANISM: Artificial
<220> FEATURE:
<223> OTHER INFORMATION: primer

<400> SEQUENCE: 11
cgtaatcatg gccatatgct gtttcctgtg tg                                   32

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
ggaattccat atgcctgccg ccgccctgca                                      30

<210> SEQ ID NO 13
<211> LENGTH: 33
<212> TYPE: DNA
<213> ORGANISM: Artificial
<220> FEATURE:

-continued

<223> OTHER INFORMATION: primer

<400> SEQUENCE: 13
aactgcagtc agcgcacgat gtagcgcagt tcg                33

<210> SEQ ID NO 14
<211> LENGTH: 1323
<212> TYPE: DNA
<213> ORGANISM: Variovorax Paradoxus
<220> FEATURE:
<221> NAME/KEY: CDS
<222> LOCATION: (1)..(1323)

<400> SEQUENCE: 14

| atg | ccc | gcc | gcc | ctc | caa | cgc | cgc | tcc | tgg | gtt | ccc | gcc | gcc | agc | gaa | 48 |
| Met | Pro | Ala | Ala | Leu | Gln | Arg | Arg | Ser | Trp | Val | Pro | Ala | Ala | Ser | Glu | |
| 1 | | | | 5 | | | | | 10 | | | | | 15 | | |

| gac | cat | gtg | ctc | gcg | atc | gcc | gcc | gat | gcc | gct | gcg | cgc | gat | gcg | ctg | 96 |
| Asp | His | Val | Leu | Ala | Ile | Ala | Ala | Asp | Ala | Ala | Ala | Arg | Asp | Ala | Leu | |
| | | | 20 | | | | | 25 | | | | | 30 | | | |

| ggc | atc | gcc | gcc | gag | atc | gaa | agg | ctc | gcc | gac | gac | aac | cac | cgc | atc | 144 |
| Gly | Ile | Ala | Ala | Glu | Ile | Glu | Arg | Leu | Ala | Asp | Asp | Asn | His | Arg | Ile | |
| | | 35 | | | | | 40 | | | | | 45 | | | | |

| cac | gac | cgc | gag | ggc | ctg | aac | ctc | aac | ccc | gcc | acc | aac | gtg | atg | aac | 192 |
| His | Asp | Arg | Glu | Gly | Leu | Asn | Leu | Asn | Pro | Ala | Thr | Asn | Val | Met | Asn | |
| 50 | | | | | 55 | | | | | 60 | | | | | | |

| ccg | gcc | gcc | gag | gcg | ctg | ctg | tcg | cgc | ggc | ctg | ggc | tcg | cgg | gca | tcg | 240 |
| Pro | Ala | Ala | Glu | Ala | Leu | Leu | Ser | Arg | Gly | Leu | Gly | Ser | Arg | Ala | Ser | |
| 65 | | | | 70 | | | | | 75 | | | | | 80 | | |

| ctg | ggc | tac | cca | ggg | gac | aag | tac | gaa | gtg | ggg | ctg | gag | gcc | atc | gag | 288 |
| Leu | Gly | Tyr | Pro | Gly | Asp | Lys | Tyr | Glu | Val | Gly | Leu | Glu | Ala | Ile | Glu | |
| | | | | 85 | | | | | 90 | | | | | 95 | | |

| cgc | atc | gag | gtc | atc | gcg | gcc | gaa | ctg | gcc | gcc | gag | gtg | ttc | ggc | tcg | 336 |
| Arg | Ile | Glu | Val | Ile | Ala | Ala | Glu | Leu | Ala | Ala | Glu | Val | Phe | Gly | Ser | |
| | | | | | 100 | | | | | 105 | | | | | 110 | |

| aag | ttc | gcc | gaa | gtg | cgc | gtg | agc | tcc | ggc | gcg | ctg | tcg | aat | ctc | tat | 384 |
| Lys | Phe | Ala | Glu | Val | Arg | Val | Ser | Ser | Gly | Ala | Leu | Ser | Asn | Leu | Tyr | |
| | | | 115 | | | | | 120 | | | | | 125 | | | |

| gtg | ttc | atg | gca | acc | tgc | cgg | ccc | ggc | gac | acg | atc | att | gcg | ccg | ccg | 432 |
| Val | Phe | Met | Ala | Thr | Cys | Arg | Pro | Gly | Asp | Thr | Ile | Ile | Ala | Pro | Pro | |
| | | 130 | | | | | 135 | | | | | 140 | | | | |

| ccg | gcc | atc | ggc | ggc | cac | gtc | acg | cac | cat | gcg | gcc | ggc | gcg | gcc | ggg | 480 |
| Pro | Ala | Ile | Gly | Gly | His | Val | Thr | His | His | Ala | Ala | Gly | Ala | Ala | Gly | |
| 145 | | | | | 150 | | | | | 155 | | | | | 160 | |

| ctc | tat | gga | ttg | aag | acg | gtg | ccc | gcg | ccg | gtc | gat | gcc | gac | ggc | tac | 528 |
| Leu | Tyr | Gly | Leu | Lys | Thr | Val | Pro | Ala | Pro | Val | Asp | Ala | Asp | Gly | Tyr | |
| | | | | 165 | | | | | 170 | | | | | 175 | | |

| acg | gtc | gac | gcg | gcc | gcg | ctc | gcc | agg | ctc | gca | cgc | gag | gtg | aag | ccg | 576 |
| Thr | Val | Asp | Ala | Ala | Ala | Leu | Ala | Arg | Leu | Ala | Arg | Glu | Val | Lys | Pro | |
| | | | | 180 | | | | | 185 | | | | | 190 | | |

| aag | ctc | atc | acc | atc | ggc | ggc | agc | ctg | aat | ctt | ttt | ccg | cac | ccg | gtg | 624 |
| Lys | Leu | Ile | Thr | Ile | Gly | Gly | Ser | Leu | Asn | Leu | Phe | Pro | His | Pro | Val | |
| | | | 195 | | | | | 200 | | | | | 205 | | | |

| cct | gcg | atc | cgc | gag | gtc | gcg | gac | agc | gtg | ggc | gcc | aaa | ctg | ctg | ttc | 672 |
| Pro | Ala | Ile | Arg | Glu | Val | Ala | Asp | Ser | Val | Gly | Ala | Lys | Leu | Leu | Phe | |
| | | 210 | | | | | 215 | | | | | 220 | | | | |

| gac | gct | gcg | cac | ctc | tcg | ggc | atg | gtg | gcc | ggc | aag | gcc | tgg | ccg | cag | 720 |
| Asp | Ala | Ala | His | Leu | Ser | Gly | Met | Val | Ala | Gly | Lys | Ala | Trp | Pro | Gln | |
| 225 | | | | | 230 | | | | | 235 | | | | | 240 | |

| ccg | ctc | gag | gag | ggc | gcg | cac | gcg | atc | acc | atg | agc | acc | tac | aag | agc | 768 |
| Pro | Leu | Glu | Glu | Gly | Ala | His | Ala | Ile | Thr | Met | Ser | Thr | Tyr | Lys | Ser | |

```
                245                 250                 255
ctc ggc gga ccg gcc ggc ggg ctg atc gtg tcg aac gat gcg gcg ctg        816
Leu Gly Gly Pro Ala Gly Gly Leu Ile Val Ser Asn Asp Ala Ala Leu
                260                 265                 270 atg gag cgc atc gac gcc atc gcc tac ccc ggc ctc acg gcc aac tcc        864
Met Glu Arg Ile Asp Ala Ile Ala Tyr Pro Gly Leu Thr Ala Asn Ser
            275                 280                 285 gat gcg ggc cgc acc gcg gcg ctg gcg cgc gga ctg ctc gac tgg aag        912
Asp Ala Gly Arg Thr Ala Ala Leu Ala Arg Gly Leu Leu Asp Trp Lys
        290                 295                 300 gtg cac ggc agg gcc tac gcc gcg gca atg cgc gag acc gcg cag gcg        960
Val His Gly Arg Ala Tyr Ala Ala Ala Met Arg Glu Thr Ala Gln Ala
305                 310                 315                 320 ctg gcg cac gcg ctc gac gcc gag ggc ttg ccg gtg ttc gcg aag gcg       1008
Leu Ala His Ala Leu Asp Ala Glu Gly Leu Pro Val Phe Ala Lys Ala
                325                 330                 335 cgc ggc ttc acg cag tcg cac cag ttc gcg ctc gag gcc gcg cac tgg       1056
Arg Gly Phe Thr Gln Ser His Gln Phe Ala Leu Glu Ala Ala His Trp
            340                 345                 350 ggc ggt ggg cag cgc gcc gcg aag aaa ctg gcc gag ggc ggt ttg ctg       1104
Gly Gly Gly Gln Arg Ala Ala Lys Lys Leu Ala Glu Gly Gly Leu Leu
        355                 360                 365 gcc tgc ggc atc ggc ctg ccg atc gcg ccg gtc gaa gga gac atc aac       1152
Ala Cys Gly Ile Gly Leu Pro Ile Ala Pro Val Glu Gly Asp Ile Asn
370                 375                 380 ggc ctg cgc ctg ggc gtg ccg gag atc gtg cgg ctg ggc ttc acg ccc       1200
Gly Leu Arg Leu Gly Val Pro Glu Ile Val Arg Leu Gly Phe Thr Pro
                390                 395                 400
385 gac gac atg ccg cag ctt gcc tcg tgg atc gcg cgt gcg ctg gag ggc       1248
Asp Asp Met Pro Gln Leu Ala Ser Trp Ile Ala Arg Ala Leu Glu Gly
            405                 410                 415 ggc ggc gca tcg gtg gcg gcc gag gtg cgc gag cgc cgc acg cgg ctc       1296
Gly Gly Ala Ser Val Ala Ala Glu Val Arg Glu Arg Arg Thr Arg Leu
        420                 425                 430 ggc ggc ctg cgc tac atc gtg cgc tga                                   1323
Gly Gly Leu Arg Tyr Ile Val Arg
            435                 440

<210> SEQ ID NO 15
<211> LENGTH: 440
<212> TYPE: PRT
<213> ORGANISM: Variovorax Paradoxus

<400> SEQUENCE: 15

Met Pro Ala Ala Leu Gln Arg Arg Ser Trp Val Pro Ala Ala Ser Glu
1               5                   10                  15

Asp His Val Leu Ala Ile Ala Ala Asp Ala Ala Ala Arg Asp Ala Leu
                20                  25                  30

Gly Ile Ala Ala Glu Ile Glu Arg Leu Ala Asp Asp Asn His Arg Ile
            35                  40                  45

His Asp Arg Glu Gly Leu Asn Leu Asn Pro Ala Thr Asn Val Met Asn
        50                  55                  60

Pro Ala Ala Glu Ala Leu Leu Ser Arg Gly Leu Gly Ser Arg Ala Ser
65                  70                  75                  80

Leu Gly Tyr Pro Gly Asp Lys Tyr Glu Val Gly Leu Glu Ala Ile Glu
                85                  90                  95

Arg Ile Glu Val Ile Ala Ala Glu Leu Ala Ala Glu Val Phe Gly Ser
            100                 105                 110
```

-continued

```
Lys Phe Ala Glu Val Arg Val Ser Ser Gly Ala Leu Ser Asn Leu Tyr
            115                 120                 125
Val Phe Met Ala Thr Cys Arg Pro Gly Asp Thr Ile Ile Ala Pro Pro
130                 135                 140
Pro Ala Ile Gly Gly His Val Thr His His Ala Gly Ala Ala Gly
145                 150                 155                 160
Leu Tyr Gly Leu Lys Thr Val Pro Ala Pro Val Asp Ala Asp Gly Tyr
            165                 170                 175
Thr Val Asp Ala Ala Ala Leu Ala Arg Leu Ala Arg Glu Val Lys Pro
            180                 185                 190
Lys Leu Ile Thr Ile Gly Gly Ser Leu Asn Leu Phe Pro His Pro Val
            195                 200                 205
Pro Ala Ile Arg Glu Val Ala Asp Ser Val Gly Ala Lys Leu Leu Phe
210                 215                 220
Asp Ala Ala His Leu Ser Gly Met Val Ala Gly Lys Ala Trp Pro Gln
225                 230                 235                 240
Pro Leu Glu Glu Gly Ala His Ala Ile Thr Met Ser Thr Tyr Lys Ser
            245                 250                 255
Leu Gly Gly Pro Ala Gly Gly Leu Ile Val Ser Asn Asp Ala Ala Leu
            260                 265                 270
Met Glu Arg Ile Asp Ala Ile Ala Tyr Pro Gly Leu Thr Ala Asn Ser
            275                 280                 285
Asp Ala Gly Arg Thr Ala Ala Leu Ala Arg Gly Leu Leu Asp Trp Lys
            290                 295                 300
Val His Gly Arg Ala Tyr Ala Ala Ala Met Arg Glu Thr Ala Gln Ala
305                 310                 315                 320
Leu Ala His Ala Leu Asp Ala Glu Gly Leu Pro Val Phe Ala Lys Ala
            325                 330                 335
Arg Gly Phe Thr Gln Ser His Gln Phe Ala Leu Glu Ala Ala His Trp
            340                 345                 350
Gly Gly Gly Gln Arg Ala Ala Lys Lys Leu Ala Glu Gly Gly Leu Leu
            355                 360                 365
Ala Cys Gly Ile Gly Leu Pro Ile Ala Pro Val Glu Gly Asp Ile Asn
370                 375                 380
Gly Leu Arg Leu Gly Val Pro Glu Ile Val Arg Leu Gly Phe Thr Pro
385                 390                 395                 400
Asp Asp Met Pro Gln Leu Ala Ser Trp Ile Ala Arg Ala Leu Glu Gly
            405                 410                 415
Gly Gly Ala Ser Val Ala Ala Glu Val Arg Glu Arg Thr Arg Leu
            420                 425                 430
Gly Gly Leu Arg Tyr Ile Val Arg
            435                 440
```

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
ggaattccat atgcccgccg ccctccaacg                                    30

<210> SEQ ID NO 17
<211> LENGTH: 33
<212> TYPE: DNA

<213> ORGANISM: Artificial
<220> FEATURE:
<223> OTHER INFORMATION: primer

<400> SEQUENCE: 17
aactgcagtc agcgcacgat gtagcgcagg ccg　　　　　　　　　　　　　　　　33

<210> SEQ ID NO 18
<211> LENGTH: 1323
<212> TYPE: DNA
<213> ORGANISM: Variovorax Paradoxus
<220> FEATURE:
<221> NAME/KEY: CDS
<222> LOCATION: (1)..(1323)

<400> SEQUENCE: 18

| atg | ccc | gca | gcc | ctt | cac | cgc | cgt | tcc | tgg | gtt | ccc | gcc | gcc | agc | gag | 48 |
|---|---|---|---|---|---|---|---|---|---|---|---|---|---|---|---|---|
| Met | Pro | Ala | Ala | Leu | His | Arg | Arg | Ser | Trp | Val | Pro | Ala | Ala | Ser | Glu | |
| 1 | | | | 5 | | | | | 10 | | | | | 15 | | |

| gac | cac | gtg | ctc | gcc | atc | gct | gcc | gac | gcc | gcg | cgc | gac | gcg | gcg | 96 |
|---|---|---|---|---|---|---|---|---|---|---|---|---|---|---|---|
| Asp | His | Val | Leu | Ala | Ile | Ala | Ala | Asp | Ala | Ala | Arg | Asp | Ala | Ala | |
| | 20 | | | | 25 | | | | | 30 | | | | | |

| ggc | gtg | gcc | gcc | gag | gtc | gaa | cgc | ctc | gtg | gcc | gac | agc | cac | cgc | atc | 144 |
|---|---|---|---|---|---|---|---|---|---|---|---|---|---|---|---|---|
| Gly | Val | Ala | Ala | Glu | Val | Glu | Arg | Leu | Val | Ala | Asp | Ser | His | Arg | Ile | |
| | 35 | | | | | 40 | | | | | 45 | | | | | |

| cac | gac | gtc | gac | ggg | ctg | aac | ctc | aac | ccc | gcc | acc | aac | gtg | atg | aac | 192 |
|---|---|---|---|---|---|---|---|---|---|---|---|---|---|---|---|---|
| His | Asp | Val | Asp | Gly | Leu | Asn | Leu | Asn | Pro | Ala | Thr | Asn | Val | Met | Asn | |
| 50 | | | | | 55 | | | | | 60 | | | | | | |

| ccc | gcc | gcc | gaa | gcg | ctg | ctg | tcg | cgc | ggg | ctg | ggc | tcg | cgt | ccg | tcg | 240 |
|---|---|---|---|---|---|---|---|---|---|---|---|---|---|---|---|---|
| Pro | Ala | Ala | Glu | Ala | Leu | Leu | Ser | Arg | Gly | Leu | Gly | Ser | Arg | Pro | Ser | |
| 65 | | | | 70 | | | | | 75 | | | | | 80 | | |

| ctg | ggc | tac | ccg | ggc | gac | aag | tac | gag | atg | ggg | ctg | gag | gcc | atc | gag | 288 |
|---|---|---|---|---|---|---|---|---|---|---|---|---|---|---|---|---|
| Leu | Gly | Tyr | Pro | Gly | Asp | Lys | Tyr | Glu | Met | Gly | Leu | Glu | Ala | Ile | Glu | |
| | | | | 85 | | | | | 90 | | | | | 95 | | |

| cgc | atc | gag | gtc | gtc | gcc | gcc | gag | ctg | gcg | gcc | gag | gtg | ttc | ggc | gcg | 336 |
|---|---|---|---|---|---|---|---|---|---|---|---|---|---|---|---|---|
| Arg | Ile | Glu | Val | Val | Ala | Ala | Glu | Leu | Ala | Ala | Glu | Val | Phe | Gly | Ala | |
| | | 100 | | | | | 105 | | | | | 110 | | | | |

| cgc | ttc | gcc | gag | gtg | cgc | gtg | agc | tcg | ggc | gcg | ctg | tcg | aac | ctc | tac | 384 |
|---|---|---|---|---|---|---|---|---|---|---|---|---|---|---|---|---|
| Arg | Phe | Ala | Glu | Val | Arg | Val | Ser | Ser | Gly | Ala | Leu | Ser | Asn | Leu | Tyr | |
| | 115 | | | | | 120 | | | | | 125 | | | | | |

| gtg | ttc | atg | gcg | acc | tgc | cag | ccc | ggc | gac | acg | atc | atc | gcg | ccg | ccg | 432 |
|---|---|---|---|---|---|---|---|---|---|---|---|---|---|---|---|---|
| Val | Phe | Met | Ala | Thr | Cys | Gln | Pro | Gly | Asp | Thr | Ile | Ile | Ala | Pro | Pro | |
| 130 | | | | | 135 | | | | | 140 | | | | | | |

| ccc | gcc | atc | ggc | ggc | cat | gtg | acg | cac | cac | gcg | gcg | ggc | gcg | gcc | ggg | 480 |
|---|---|---|---|---|---|---|---|---|---|---|---|---|---|---|---|---|
| Pro | Ala | Ile | Gly | Gly | His | Val | Thr | His | His | Ala | Ala | Gly | Ala | Ala | Gly | |
| 145 | | | | | 150 | | | | | 155 | | | | | 160 | |

| ctc | tac | ggc | ctg | aag | acc | gtg | ccg | gcg | ccg | gtc | gat | gcc | gac | ggc | tac | 528 |
|---|---|---|---|---|---|---|---|---|---|---|---|---|---|---|---|---|
| Leu | Tyr | Gly | Leu | Lys | Thr | Val | Pro | Ala | Pro | Val | Asp | Ala | Asp | Gly | Tyr | |
| | | | | 165 | | | | | 170 | | | | | 175 | | |

| tcg | gtc | gac | gtg | gtg | gcg | ctg | gcg | aaa | ctg | gcg | cgc | gag | gtg | aag | ccg | 576 |
|---|---|---|---|---|---|---|---|---|---|---|---|---|---|---|---|---|
| Ser | Val | Asp | Val | Val | Ala | Leu | Ala | Lys | Leu | Ala | Arg | Glu | Val | Lys | Pro | |
| | | 180 | | | | | 185 | | | | | 190 | | | | |

| aag | ctc | atc | acc | atc | ggc | ggc | agc | ctc | aac | ctg | ttc | ccg | cac | ccg | gtg | 624 |
|---|---|---|---|---|---|---|---|---|---|---|---|---|---|---|---|---|
| Lys | Leu | Ile | Thr | Ile | Gly | Gly | Ser | Leu | Asn | Leu | Phe | Pro | His | Pro | Val | |
| | 195 | | | | | 200 | | | | | 205 | | | | | |

| ccc | gcg | atc | cgc | gag | gtg | gcc | gac | agc | gtg | ggc | gcc | aag | gtg | ctc | ttc | 672 |
|---|---|---|---|---|---|---|---|---|---|---|---|---|---|---|---|---|
| Pro | Ala | Ile | Arg | Glu | Val | Ala | Asp | Ser | Val | Gly | Ala | Lys | Val | Leu | Phe | |
| 210 | | | | | 215 | | | | | 220 | | | | | | |

| gat | gcc | gcg | cac | ctc | tcg | ggc | atg | gtg | gcc | ggc | aag | gct | tgg | ccg | cag | 720 |
|---|---|---|---|---|---|---|---|---|---|---|---|---|---|---|---|---|
| Asp | Ala | Ala | His | Leu | Ser | Gly | Met | Val | Ala | Gly | Lys | Ala | Trp | Pro | Gln | |
| 225 | | | | | 230 | | | | | 235 | | | | | 240 | |

```
ccg ctc gaa gac ggc gcg cac gcg atc acg atg agc acc tac aag agc    768
Pro Leu Glu Asp Gly Ala His Ala Ile Thr Met Ser Thr Tyr Lys Ser
            245                 250                 255 ctg ggc ggc ccg gcc ggc ggg ctg atc gtg tcg aac gat gcg gcg ctg    816
Leu Gly Gly Pro Ala Gly Gly Leu Ile Val Ser Asn Asp Ala Ala Leu
        260                 265                 270 atg gag cgc atc gac gcc atc gcc tac ccc ggc ctc acg gcc aac tcg    864
Met Glu Arg Ile Asp Ala Ile Ala Tyr Pro Gly Leu Thr Ala Asn Ser
    275                 280                 285 gac gcg ggc cgc acc gcg gcg ctg gcg cgc ggt ctg ctc gac tgg aag    912
Asp Ala Gly Arg Thr Ala Ala Leu Ala Arg Gly Leu Leu Asp Trp Lys
290                 295                 300 gtg cac ggc acg gcc tat gcg gcg gcg atg cgc gac acc gcg cag gcg    960
Val His Gly Thr Ala Tyr Ala Ala Ala Met Arg Asp Thr Ala Gln Ala
305                 310                 315                 320 ctg gca cgc gcg ctc gat gcc cta ggc ctg ccg gtg ttc gcc aag gca    1008
Leu Ala Arg Ala Leu Asp Ala Leu Gly Leu Pro Val Phe Ala Lys Ala
            325                 330                 335 cgc ggc ttc acg cag tcg cac cag ttc gcg ctc gag gct gcg cgc tgg    1056
Arg Gly Phe Thr Gln Ser His Gln Phe Ala Leu Glu Ala Ala Arg Trp
        340                 345                 350 ggc ggc ggg caa cgc gcc gcg aag cag ctg gcc cgg ggc ggg ttg ttg    1104
Gly Gly Gly Gln Arg Ala Ala Lys Gln Leu Ala Arg Gly Gly Leu Leu
    355                 360                 365 gcc tgc ggc atc ggc ctg ccg atc gca ccg gtc gac ggc gac atc aac    1152
Ala Cys Gly Ile Gly Leu Pro Ile Ala Pro Val Asp Gly Asp Ile Asn
370                 375                 380 ggc ctg cgc ctg ggc gtg ccc gag atc gtg cgg ctg ggc ttc acg ccc    1200
Gly Leu Arg Leu Gly Val Pro Glu Ile Val Arg Leu Gly Phe Thr Pro
385                 390                 395                 400 gag gac atg ccg caa ctg gcc ggc tgg atc gcg cgg gca ttg gct ggc    1248
Glu Asp Met Pro Gln Leu Ala Gly Trp Ile Ala Arg Ala Leu Ala Gly
            405                 410                 415 gat gcg ccc gcc gtg gcc gcc gag gtg cgc gag cgg cgc acg cgg ctg    1296
Asp Ala Pro Ala Val Ala Ala Glu Val Arg Glu Arg Arg Thr Arg Leu
        420                 425                 430 aac ggc ctg cgc tac atc gtg cgc tga                                1323
Asn Gly Leu Arg Tyr Ile Val Arg
    435                 440

<210> SEQ ID NO 19
<211> LENGTH: 440
<212> TYPE: PRT
<213> ORGANISM: Variovorax Paradoxus

<400> SEQUENCE: 19

Met Pro Ala Ala Leu His Arg Arg Ser Trp Val Pro Ala Ala Ser Glu
1               5                   10                  15

Asp His Val Leu Ala Ile Ala Ala Asp Ala Ala Arg Asp Ala Ala
            20                  25                  30

Gly Val Ala Ala Glu Val Glu Arg Leu Val Ala Asp Ser His Arg Ile
        35                  40                  45

His Asp Val Asp Gly Leu Asn Leu Asn Pro Ala Thr Asn Val Met Asn
    50                  55                  60

Pro Ala Ala Glu Ala Leu Leu Ser Arg Gly Leu Gly Ser Arg Pro Ser
65                  70                  75                  80

Leu Gly Tyr Pro Gly Asp Lys Tyr Glu Met Gly Leu Glu Ala Ile Glu
                85                  90                  95

Arg Ile Glu Val Val Ala Ala Glu Leu Ala Ala Glu Val Phe Gly Ala
```

```
                100             105             110
Arg Phe Ala Glu Val Arg Val Ser Ser Gly Ala Leu Ser Asn Leu Tyr
            115                 120                 125
Val Phe Met Ala Thr Cys Gln Pro Gly Asp Thr Ile Ile Ala Pro Pro
        130                 135                 140
Pro Ala Ile Gly Gly His Val Thr His His Ala Ala Gly Ala Ala Gly
145                 150                 155                 160
Leu Tyr Gly Leu Lys Thr Val Pro Ala Pro Val Asp Ala Asp Gly Tyr
                165                 170                 175
Ser Val Asp Val Val Ala Leu Ala Lys Leu Ala Arg Glu Val Lys Pro
            180                 185                 190
Lys Leu Ile Thr Ile Gly Gly Ser Leu Asn Leu Phe Pro His Pro Val
        195                 200                 205
Pro Ala Ile Arg Glu Val Ala Asp Ser Val Gly Ala Lys Val Leu Phe
    210                 215                 220
Asp Ala Ala His Leu Ser Gly Met Val Ala Gly Lys Ala Trp Pro Gln
225                 230                 235                 240
Pro Leu Glu Asp Gly Ala His Ala Ile Thr Met Ser Thr Tyr Lys Ser
                245                 250                 255
Leu Gly Gly Pro Ala Gly Gly Leu Ile Val Ser Asn Asp Ala Ala Leu
            260                 265                 270
Met Glu Arg Ile Asp Ala Ile Ala Tyr Pro Gly Leu Thr Ala Asn Ser
        275                 280                 285
Asp Ala Gly Arg Thr Ala Ala Leu Ala Arg Gly Leu Leu Asp Trp Lys
    290                 295                 300
Val His Gly Thr Ala Tyr Ala Ala Ala Met Arg Asp Thr Ala Gln Ala
305                 310                 315                 320
Leu Ala Arg Ala Leu Asp Ala Leu Gly Leu Pro Val Phe Ala Lys Ala
                325                 330                 335
Arg Gly Phe Thr Gln Ser His Gln Phe Ala Leu Glu Ala Ala Arg Trp
            340                 345                 350
Gly Gly Gly Gln Arg Ala Ala Lys Gln Leu Ala Arg Gly Gly Leu Leu
        355                 360                 365
Ala Cys Gly Ile Gly Leu Pro Ile Ala Pro Val Asp Gly Asp Ile Asn
    370                 375                 380
Gly Leu Arg Leu Gly Val Pro Glu Ile Val Arg Leu Gly Phe Thr Pro
385                 390                 395                 400
Glu Asp Met Pro Gln Leu Ala Gly Trp Ile Ala Arg Ala Leu Ala Gly
                405                 410                 415
Asp Ala Pro Ala Val Ala Ala Glu Val Arg Glu Arg Thr Arg Leu
            420                 425                 430
Asn Gly Leu Arg Tyr Ile Val Arg
        435                 440

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
ggaattccat atgcccgcag cccttcaccg                                      30

<210> SEQ ID NO 21
```

-continued

```
<211> LENGTH: 33
<212> TYPE: DNA
<213> ORGANISM: Artificial
<220> FEATURE:
<223> OTHER INFORMATION: primer

<400> SEQUENCE: 21
aactgcagtc agcgcacgat gtagcgcagg ccg                                    33

<210> SEQ ID NO 22
<211> LENGTH: 1323
<212> TYPE: DNA
<213> ORGANISM: Bosa sp.
<220> FEATURE:
<221> NAME/KEY: CDS
<222> LOCATION: (1)..(1323)

<400> SEQUENCE: 22
```

| | | | | | | | | | | | | | | | | |
|---|---|---|---|---|---|---|---|---|---|---|---|---|---|---|---|---|
| atg | acg | gct | ctg | ggc | agg | cgc | gat | tgg | gtg | ccg | cag | gcg | agc | gag | gac | 48 |
| Met | Thr | Ala | Leu | Gly | Arg | Arg | Asp | Trp | Val | Pro | Gln | Ala | Ser | Glu | Asp | |
| 1 | | | | 5 | | | | | 10 | | | | | 15 | | |
| tat | atc | cag | cgg | atc | gcc | ggc | gag | acg | gcg | ggc | cag | ccg | ctc | gat | gcc | 96 |
| Tyr | Ile | Gln | Arg | Ile | Ala | Gly | Glu | Thr | Ala | Gly | Gln | Pro | Leu | Asp | Ala | |
| | | | 20 | | | | | 25 | | | | | 30 | | | |
| atc | gcg | gac | agg | att | acg | gcg | ctg | acc | gcc | gag | aac | cgc | gcc | atc | cac | 144 |
| Ile | Ala | Asp | Arg | Ile | Thr | Ala | Leu | Thr | Ala | Glu | Asn | Arg | Ala | Ile | His | |
| | | 35 | | | | | 40 | | | | | 45 | | | | |
| gag | cgc | gat | tgc | gtc | aat | ctc | aac | ccg | gcc | acc | aat | gtc | atg | aac | ccg | 192 |
| Glu | Arg | Asp | Cys | Val | Asn | Leu | Asn | Pro | Ala | Thr | Asn | Val | Met | Asn | Pro | |
| 50 | | | | | 55 | | | | | 60 | | | | | | |
| aag | gcc | gag | gcg | ctg | ctc | tcg | gcg | ggg | atc | ggg | gcg | cgg | ccc | tcg | ctc | 240 |
| Lys | Ala | Glu | Ala | Leu | Leu | Ser | Ala | Gly | Ile | Gly | Ala | Arg | Pro | Ser | Leu | |
| 65 | | | | | 70 | | | | | 75 | | | | | 80 | |
| ggc | tat | ccc | ggc | gac | aaa | tac | gag | atg | ggg | ctg | gag | gcg | atc | gag | cag | 288 |
| Gly | Tyr | Pro | Gly | Asp | Lys | Tyr | Glu | Met | Gly | Leu | Glu | Ala | Ile | Glu | Gln | |
| | | | | 85 | | | | | 90 | | | | | 95 | | |
| atc | gag | gtg | atc | gcg | gcc | gag | ctc | gca | gcc | gag | gtt | ttc | ggc | gcg | aca | 336 |
| Ile | Glu | Val | Ile | Ala | Ala | Glu | Leu | Ala | Ala | Glu | Val | Phe | Gly | Ala | Thr | |
| | | | 100 | | | | | 105 | | | | | 110 | | | |
| tat | gcg | gag | atc | cgc | gtg | ccc | tcc | ggc | gcc | atc | gcc | aat | ctc | tac | gcc | 384 |
| Tyr | Ala | Glu | Ile | Arg | Val | Pro | Ser | Gly | Ala | Ile | Ala | Asn | Leu | Tyr | Ala | |
| | | 115 | | | | | 120 | | | | | 125 | | | | |
| ttc | atg | gtt | gcg | gcg | aag | gcg | ggc | gac | tgc | atc | atc | gcg | ccg | ccg | ggc | 432 |
| Phe | Met | Val | Ala | Ala | Lys | Ala | Gly | Asp | Cys | Ile | Ile | Ala | Pro | Pro | Gly | |
| | | 130 | | | | | 135 | | | | | 140 | | | | |
| gag | atc | ggc | ggg | cat | gtc | acc | cat | cac | ggc | gcg | ggc | gcg | gcc | ggg | ctc | 480 |
| Glu | Ile | Gly | Gly | His | Val | Thr | His | His | Gly | Ala | Gly | Ala | Ala | Gly | Leu | |
| 145 | | | | | 150 | | | | | 155 | | | | | 160 | |
| tac | ggc | atc | att | acc | cat | ccg | gcg | ccg | atc | gac | ccc | gtg | aag | tat | acg | 528 |
| Tyr | Gly | Ile | Ile | Thr | His | Pro | Ala | Pro | Ile | Asp | Pro | Val | Lys | Tyr | Thr | |
| | | | | 165 | | | | | 170 | | | | | 175 | | |
| gtc | gat | gtc | gaa | aag | ctg | cgc | gcg | gac | gcg | ctc | agg | ctc | cgg | ccg | aag | 576 |
| Val | Asp | Val | Glu | Lys | Leu | Arg | Ala | Asp | Ala | Leu | Arg | Leu | Arg | Pro | Lys | |
| | | | | 180 | | | | | 185 | | | | | 190 | | |
| ctg | atc | tcg | atc | ggc | ggc | agc | ctc | aat | ctc | ttc | ccg | cat | ccg | atc | cgc | 624 |
| Leu | Ile | Ser | Ile | Gly | Gly | Ser | Leu | Asn | Leu | Phe | Pro | His | Pro | Ile | Arg | |
| | | | 195 | | | | | 200 | | | | | 205 | | | |
| gag | atc | cgc | acc | atc | gcc | gac | gag | gtc | ggt | gcg | ctc | gtg | ctg | ttc | gac | 672 |
| Glu | Ile | Arg | Thr | Ile | Ala | Asp | Glu | Val | Gly | Ala | Leu | Val | Leu | Phe | Asp | |
| | | 210 | | | | | 215 | | | | | 220 | | | | |
| gcg | gcg | cat | atg | tcc | ggc | atg | atc | gcc | ggc | cat | ggc | tgg | cag | cag | ccg | 720 |
| Ala | Ala | His | Met | Ser | Gly | Met | Ile | Ala | Gly | His | Gly | Trp | Gln | Gln | Pro | |

```
                                                                                                    -continued
        225                     230                     235                     240
ctg gag gag ggt gct cat ctg atg acg atg agc acc tat aag agc ctc                                     768
Leu Glu Glu Gly Ala His Leu Met Thr Met Ser Thr Tyr Lys Ser Leu
                    245                     250                     255 ggc ggg ccg cct tca ggg ttg atc gtc acc aat gat gcc gac atc gcg                                     816
Gly Gly Pro Pro Ser Gly Leu Ile Val Thr Asn Asp Ala Asp Ile Ala
            260                     265                     270 aaa aaa ctc gac gcc atc gcc tat ccc ggg ctc acc gcc aat ttc gat                                     864
Lys Lys Leu Asp Ala Ile Ala Tyr Pro Gly Leu Thr Ala Asn Phe Asp
        275                     280                     285 gca gcc aag tcg gcg tcg ctg gcc gtc tcg ctc ctc gat tgg aaa gca                                     912
Ala Ala Lys Ser Ala Ser Leu Ala Val Ser Leu Leu Asp Trp Lys Ala
    290                     295                     300 cat ggc cgc gcc tat gcg cag gag atg gcc aag aca gcg aag gcc ttg                                     960
His Gly Arg Ala Tyr Ala Gln Glu Met Ala Lys Thr Ala Lys Ala Leu
305                     310                     315                     320 gcc gag gct ctg tca gag cgg cag gtg ccg gtt ttc gcc cgc gac cgg                                     1008
Ala Glu Ala Leu Ser Glu Arg Gln Val Pro Val Phe Ala Arg Asp Arg
                    325                     330                     335 ggc atg acg acc tcg cat cag ttc gcc atc gaa gcc gcg ccc tat ggc                                     1056
Gly Met Thr Thr Ser His Gln Phe Ala Ile Glu Ala Ala Pro Tyr Gly
            340                     345                     350 ggt ggg cag gcg gca gcg aag cgg ctt cgc gcg gtc aac atc ctg tcc                                     1104
Gly Gly Gln Ala Ala Ala Lys Arg Leu Arg Ala Val Asn Ile Leu Ser
        355                     360                     365 tgc ggc atc ggc ctg ccg ctg ccg gcg gtg gag ggc gat gtg aac ggg                                     1152
Cys Gly Ile Gly Leu Pro Leu Pro Ala Val Glu Gly Asp Val Asn Gly
    370                     375                     380 ctc agg ctc ggc acg ccg gag atc gtg cgc ttt ggc atg acg gcc gcc                                     1200
Leu Arg Leu Gly Thr Pro Glu Ile Val Arg Phe Gly Met Thr Ala Ala
385                     390                     395                     400 gac atg ccg gag ctg gcg ggt tat atc gcc gag ggg ttg aac ggc tcg                                     1248
Asp Met Pro Glu Leu Ala Gly Tyr Ile Ala Glu Gly Leu Asn Gly Ser
                    405                     410                     415 cgt ccg gcc gag gcg gtg gcg aag gac gtg acg gca ttc cgc ggc cgc                                     1296
Arg Pro Ala Glu Ala Val Ala Lys Asp Val Thr Ala Phe Arg Gly Arg
            420                     425                     430 ttc cgc gag ctg cat ttc atg cgc tga                                                                 1323
Phe Arg Glu Leu His Phe Met Arg
        435                     440

<210> SEQ ID NO 23
<211> LENGTH: 440
<212> TYPE: PRT
<213> ORGANISM: Bosa sp.

<400> SEQUENCE: 23

Met Thr Ala Leu Gly Arg Arg Asp Trp Val Pro Gln Ala Ser Glu Asp
1               5                   10                  15

Tyr Ile Gln Arg Ile Ala Gly Glu Thr Ala Gly Gln Pro Leu Asp Ala
                20                  25                  30

Ile Ala Asp Arg Ile Thr Ala Leu Thr Ala Glu Asn Arg Ala Ile His
        35                  40                  45

Glu Arg Asp Cys Val Asn Leu Asn Pro Ala Thr Asn Val Met Asn Pro
    50                  55                  60

Lys Ala Glu Ala Leu Leu Ser Ala Gly Ile Gly Ala Arg Pro Ser Leu
65                  70                  75                  80

Gly Tyr Pro Gly Asp Lys Tyr Glu Met Gly Leu Glu Ala Ile Glu Gln
                85                  90                  95
```

-continued

```
Ile Glu Val Ile Ala Ala Glu Leu Ala Ala Glu Val Phe Gly Ala Thr
            100                 105                 110
Tyr Ala Glu Ile Arg Val Pro Ser Gly Ala Ile Ala Asn Leu Tyr Ala
        115                 120                 125
Phe Met Val Ala Ala Lys Ala Gly Asp Cys Ile Ile Ala Pro Pro Gly
130                 135                 140
Glu Ile Gly Gly His Val Thr His Gly Ala Gly Ala Ala Gly Leu
145                 150                 155                 160
Tyr Gly Ile Ile Thr His Pro Ala Pro Ile Asp Pro Val Lys Tyr Thr
                165                 170                 175
Val Asp Val Glu Lys Leu Arg Ala Asp Ala Leu Arg Leu Arg Pro Lys
            180                 185                 190
Leu Ile Ser Ile Gly Gly Ser Leu Asn Leu Phe Pro His Pro Ile Arg
        195                 200                 205
Glu Ile Arg Thr Ile Ala Asp Glu Val Gly Ala Leu Val Leu Phe Asp
    210                 215                 220
Ala Ala His Met Ser Gly Met Ile Ala Gly His Gly Trp Gln Gln Pro
225                 230                 235                 240
Leu Glu Glu Gly Ala His Leu Met Thr Met Ser Thr Tyr Lys Ser Leu
                245                 250                 255
Gly Gly Pro Pro Ser Gly Leu Ile Val Thr Asn Asp Ala Asp Ile Ala
            260                 265                 270
Lys Lys Leu Asp Ala Ile Ala Tyr Pro Gly Leu Thr Ala Asn Phe Asp
        275                 280                 285
Ala Ala Lys Ser Ala Ser Leu Ala Val Ser Leu Leu Asp Trp Lys Ala
290                 295                 300
His Gly Arg Ala Tyr Ala Gln Glu Met Ala Lys Thr Ala Lys Ala Leu
305                 310                 315                 320
Ala Glu Ala Leu Ser Glu Arg Gln Val Pro Val Phe Ala Arg Asp Arg
                325                 330                 335
Gly Met Thr Thr Ser His Gln Phe Ala Ile Glu Ala Ala Pro Tyr Gly
            340                 345                 350
Gly Gly Gln Ala Ala Lys Arg Leu Arg Ala Val Asn Ile Leu Ser
        355                 360                 365
Cys Gly Ile Gly Leu Pro Leu Pro Ala Val Glu Gly Asp Val Asn Gly
    370                 375                 380
Leu Arg Leu Gly Thr Pro Glu Ile Val Arg Phe Gly Met Thr Ala Ala
385                 390                 395                 400
Asp Met Pro Glu Leu Ala Gly Tyr Ile Ala Glu Gly Leu Asn Gly Ser
                405                 410                 415
Arg Pro Ala Glu Ala Val Ala Lys Asp Val Thr Ala Phe Arg Gly Arg
            420                 425                 430
Phe Arg Glu Leu His Phe Met Arg
        435                 440
```

<210> SEQ ID NO 24
<211> LENGTH: 28
<212> TYPE: DNA
<213> ORGANISM: Artificial
<220> FEATURE:
<223> OTHER INFORMATION: primer

<400> SEQUENCE: 24
ggggattaat gacggctctg ggcaggcg                                    28

<210> SEQ ID NO 25
<211> LENGTH: 28
<212> TYPE: DNA
<213> ORGANISM: Artificial
<220> FEATURE:
<223> OTHER INFORMATION: primer

<400> SEQUENCE: 25
aactgcagtc agcgcatgaa atgcagct                                      28

<210> SEQ ID NO 26
<211> LENGTH: 28
<212> TYPE: DNA
<213> ORGANISM: Artificial
<220> FEATURE:
<223> OTHER INFORMATION: primer

<400> SEQUENCE: 26
ccgaattcgg aggatggggc atgacggc                                      28

<210> SEQ ID NO 27
<211> LENGTH: 33
<212> TYPE: DNA
<213> ORGANISM: Artificial
<220> FEATURE:
<223> OTHER INFORMATION: primer

<400> SEQUENCE: 27
ccgaattcag gcagagatac ggaggatccc atg                                33

<210> SEQ ID NO 28
<211> LENGTH: 34
<212> TYPE: DNA
<213> ORGANISM: Artificial
<220> FEATURE:
<223> OTHER INFORMATION: primer

<400> SEQUENCE: 28
aactgcagtc acgacctgat atggtgcatc ccct                               34

<210> SEQ ID NO 29
<211> LENGTH: 1323
<212> TYPE: DNA
<213> ORGANISM: Silicibacter pomeroyi
<220> FEATURE:
<221> NAME/KEY: CDS
<222> LOCATION: (1)..(1323)

<400> SEQUENCE: 29

```
atg cca cag ctt gcc gcc cgc ccc tgg gtg ccc gcc cat tgc gaa acc      48
Met Pro Gln Leu Ala Ala Arg Pro Trp Val Pro Ala His Cys Glu Thr
1               5                   10                  15 cgc gtt cag caa atc gcc gag acc acg gca cgc gcc gac agc gat gcc      96
Arg Val Gln Gln Ile Ala Glu Thr Thr Ala Arg Ala Asp Ser Asp Ala
            20                  25                  30 atc gac gcc cac ctg gag gcg ctg atc gaa gag aac cgc acc atc cat     144
Ile Asp Ala His Leu Glu Ala Leu Ile Glu Glu Asn Arg Thr Ile His
        35                  40                  45 gac gcg gaa tgt ttc aac ctg aac ccg gca acc aat gtt atg aac ccg     192
Asp Ala Glu Cys Phe Asn Leu Asn Pro Ala Thr Asn Val Met Asn Pro
    50                  55                  60 cgc gcc gag gcg gtg ctg gcg cgg gga ttg ggc agc cgc ccc tcg ctg     240
Arg Ala Glu Ala Val Leu Ala Arg Gly Leu Gly Ser Arg Pro Ser Leu
65                  70                  75                  80
```

-continued

```
ggc tat ccc ggc gac aaa tac gag atg ggg ctg gag gcg atc gaa gag      288
Gly Tyr Pro Gly Asp Lys Tyr Glu Met Gly Leu Glu Ala Ile Glu Glu
             85                  90                  95 atc gag gtg att gcc gca gaa ctg gcg gca aag gtg ttc aac gcg cgc      336
Ile Glu Val Ile Ala Ala Glu Leu Ala Ala Lys Val Phe Asn Ala Arg
        100                 105                 110 tat gcc gag atc cgg gtg ggc tcg ggc gcg ctc gcc aat ctt tat ggc      384
Tyr Ala Glu Ile Arg Val Gly Ser Gly Ala Leu Ala Asn Leu Tyr Gly
    115                 120                 125 ttc atg gcg ctg acc cgg ccc ggc gat acg atc atc gcg cca ccg gcc      432
Phe Met Ala Leu Thr Arg Pro Gly Asp Thr Ile Ile Ala Pro Pro Ala
130                 135                 140 agt atc ggt ggc cat gta acc cat cac aag gcg ggc tgt gcg ggg ctt      480
Ser Ile Gly Gly His Val Thr His His Lys Ala Gly Cys Ala Gly Leu
145                 150                 155                 160 tat ggc cta aaa acc atc gag gcg ccg gtg gat gcg gat ggt tac agc      528
Tyr Gly Leu Lys Thr Ile Glu Ala Pro Val Asp Ala Asp Gly Tyr Ser
                165                 170                 175 ctg gat ttg agc gcg ctg gca gag ttg gca gag cgg cac cgg ccc cgg      576
Leu Asp Leu Ser Ala Leu Ala Glu Leu Ala Glu Arg His Arg Pro Arg
            180                 185                 190 ctg atc acg gtg ggc ggc tcg ctc aac ctg ttt ccg cat cca gtt gca      624
Leu Ile Thr Val Gly Gly Ser Leu Asn Leu Phe Pro His Pro Val Ala
        195                 200                 205 gcc gtg cgc gag att gcc gac agg gtt ggt gcc aag gtt ctg ttc gac      672
Ala Val Arg Glu Ile Ala Asp Arg Val Gly Ala Lys Val Leu Phe Asp
    210                 215                 220 gcg gcg cat caa tgc ggc atc atc gcg ggc ggc gcc tgg gcc aac ccg      720
Ala Ala His Gln Cys Gly Ile Ile Ala Gly Gly Ala Trp Ala Asn Pro
225                 230                 235                 240 ctg gac gag ggg gcg cat ctg atg acg atg agc acc tac aag agc ctc      768
Leu Asp Glu Gly Ala His Leu Met Thr Met Ser Thr Tyr Lys Ser Leu
                245                 250                 255 ggc ggc cct gcc ggc ggg ctg att gtg acc aac gag gcc gag atc gcc      816
Gly Gly Pro Ala Gly Gly Leu Ile Val Thr Asn Glu Ala Glu Ile Ala
            260                 265                 270 gaa cgg ctg gac gcc atc gcc ttt ccc ggc atg acc gcg aat ttc gac      864
Glu Arg Leu Asp Ala Ile Ala Phe Pro Gly Met Thr Ala Asn Phe Asp
        275                 280                 285 gcg gcg aaa tcg gcg gcg ttg gcg atc tcg ctg ttg gac tgg gtc gat      912
Ala Ala Lys Ser Ala Ala Leu Ala Ile Ser Leu Leu Asp Trp Val Asp
    290                 295                 300 cat ggc gcg gct tat gcc cag gcc atg gtc gat ctg gcg cag gcg ctg      960
His Gly Ala Ala Tyr Ala Gln Ala Met Val Asp Leu Ala Gln Ala Leu
305                 310                 315                 320 gcc gcc gag ttg gag gcg ctg ggc ctg ccg gtg ttt cat ggc gcg ggc     1008
Ala Ala Glu Leu Glu Ala Leu Gly Leu Pro Val Phe His Gly Ala Gly
                325                 330                 335 ggg gcc acc gcc tcg cac cag ttc gcg gtc gag gcg gcg cgg ttc ggc     1056
Gly Ala Thr Ala Ser His Gln Phe Ala Val Glu Ala Ala Arg Phe Gly
            340                 345                 350 ggc ggt cag gcg gcg tcc aag acg ctg agg cgg gca ggc ttc ctg gcc     1104
Gly Gly Gln Ala Ala Ser Lys Thr Leu Arg Arg Ala Gly Phe Leu Ala
        355                 360                 365 tgt ggc atc ggc ctg ccg atc gcg ccg gtt gcg ggg gat atg aac ggc     1152
Cys Gly Ile Gly Leu Pro Ile Ala Pro Val Ala Gly Asp Met Asn Gly
    370                 375                 380 ctt cgg atc ggc acg ccg gag ctg gtg cgc cga ggg gtc acg cca gag     1200
Leu Arg Ile Gly Thr Pro Glu Leu Val Arg Arg Gly Val Thr Pro Glu
385                 390                 395                 400
```

```
cat gcc gcc gaa ctg gcc tgg ctg atc acc caa ggt ctc acc ggc aac      1248
His Ala Ala Glu Leu Ala Trp Leu Ile Thr Gln Gly Leu Thr Gly Asn
                405                 410                 415 gat ccc gaa gcg gtg gcg ctg cgc acg cgt gag atg cgg gcg cgg ttt      1296
Asp Pro Glu Ala Val Ala Leu Arg Thr Arg Glu Met Arg Ala Arg Phe
            420                 425                 430 cag ggg atg cac cat atc agg tcg tga                                  1323
Gln Gly Met His His Ile Arg Ser
        435                 440

<210> SEQ ID NO 30
<211> LENGTH: 440
<212> TYPE: PRT
<213> ORGANISM: Silicibacter pomeroyi

<400> SEQUENCE: 30

Met Pro Gln Leu Ala Ala Arg Pro Trp Val Pro Ala His Cys Glu Thr
1               5                   10                  15

Arg Val Gln Gln Ile Ala Glu Thr Thr Ala Arg Ala Asp Ser Asp Ala
            20                  25                  30

Ile Asp Ala His Leu Glu Ala Leu Ile Glu Glu Asn Arg Thr Ile His
        35                  40                  45

Asp Ala Glu Cys Phe Asn Leu Asn Pro Ala Thr Asn Val Met Asn Pro
    50                  55                  60

Arg Ala Glu Ala Val Leu Ala Arg Gly Leu Gly Ser Arg Pro Ser Leu
65                  70                  75                  80

Gly Tyr Pro Gly Asp Lys Tyr Glu Met Gly Leu Glu Ala Ile Glu Glu
                85                  90                  95

Ile Glu Val Ile Ala Ala Glu Leu Ala Ala Lys Val Phe Asn Ala Arg
            100                 105                 110

Tyr Ala Glu Ile Arg Val Gly Ser Gly Ala Leu Ala Asn Leu Tyr Gly
        115                 120                 125

Phe Met Ala Leu Thr Arg Pro Gly Asp Thr Ile Ile Ala Pro Pro Ala
    130                 135                 140

Ser Ile Gly Gly His Val Thr His His Lys Ala Gly Cys Ala Gly Leu
145                 150                 155                 160

Tyr Gly Leu Lys Thr Ile Glu Ala Pro Val Asp Ala Asp Gly Tyr Ser
                165                 170                 175

Leu Asp Leu Ser Ala Leu Ala Glu Leu Ala Glu Arg His Arg Pro Arg
            180                 185                 190

Leu Ile Thr Val Gly Gly Ser Leu Asn Leu Phe Pro His Pro Val Ala
        195                 200                 205

Ala Val Arg Glu Ile Ala Asp Arg Val Gly Ala Lys Val Leu Phe Asp
    210                 215                 220

Ala Ala His Gln Cys Gly Ile Ile Ala Gly Ala Trp Ala Asn Pro
225                 230                 235                 240

Leu Asp Glu Gly Ala His Leu Met Thr Met Ser Thr Tyr Lys Ser Leu
                245                 250                 255

Gly Gly Pro Ala Gly Gly Leu Ile Val Thr Asn Glu Ala Glu Ile Ala
            260                 265                 270

Glu Arg Leu Asp Ala Ile Ala Phe Pro Gly Met Thr Ala Asn Phe Asp
        275                 280                 285

Ala Ala Lys Ser Ala Ala Leu Ala Ile Ser Leu Leu Asp Trp Val Asp
    290                 295                 300

His Gly Ala Ala Tyr Ala Gln Ala Met Val Asp Leu Ala Gln Ala Leu
```

```
            305                 310                 315                 320
Ala Ala Glu Leu Glu Ala Leu Gly Leu Pro Val Phe His Gly Ala Gly
                325                 330                 335

Gly Ala Thr Ala Ser His Gln Phe Ala Val Glu Ala Ala Arg Phe Gly
            340                 345                 350

Gly Gly Gln Ala Ala Ser Lys Thr Leu Arg Arg Ala Gly Phe Leu Ala
        355                 360                 365

Cys Gly Ile Gly Leu Pro Ile Ala Pro Val Ala Gly Asp Met Asn Gly
    370                 375                 380

Leu Arg Ile Gly Thr Pro Glu Leu Val Arg Arg Gly Val Thr Pro Glu
385                 390                 395                 400

His Ala Ala Glu Leu Ala Trp Leu Ile Thr Gln Gly Leu Thr Gly Asn
                405                 410                 415

Asp Pro Glu Ala Val Ala Leu Arg Thr Arg Glu Met Arg Ala Arg Phe
            420                 425                 430

Gln Gly Met His His Ile Arg Ser
        435                 440

<210> SEQ ID NO 31
<211> LENGTH: 40
<212> TYPE: DNA
<213> ORGANISM: Artificial
<220> FEATURE:
<223> OTHER INFORMATION: primer

<400> SEQUENCE: 31
gtatcacgag gccctagctg tggtgtcatg gtcggtgatc                    40

<210> SEQ ID NO 32
<211> LENGTH: 40
<212> TYPE: DNA
<213> ORGANISM: Artificial
<220> FEATURE:
<223> OTHER INFORMATION: primer

<400> SEQUENCE: 32
ttcggggatt ccatatgata ccctttttac gtgaacttgc                    40

<210> SEQ ID NO 33
<211> LENGTH: 38
<212> TYPE: DNA
<213> ORGANISM: Artificial
<220> FEATURE:
<223> OTHER INFORMATION: primer

<400> SEQUENCE: 33
ggggggggca tatgcgacct ccttattacg tgaacttg                      38

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
ccggatccat gccacagctt gccgcccgcc                               30
```